United States Patent
Pieribone

(10) Patent No.: US 8,445,218 B2
(45) Date of Patent: May 21, 2013

(54) DEVICE AND METHODS FOR THE IMMUNOLOGICAL IDENTIFICATION OF CEREBROSPINAL FLUID

(75) Inventor: Vincent Pieribone, New Haven, CT (US)

(73) Assignee: Affinimark Technologies, Inc., Ellington, CT (US)

( * ) Notice: Subject to any disclaimer, the term of this patent is extended or adjusted under 35 U.S.C. 154(b) by 275 days.

(21) Appl. No.: 12/852,761

(22) Filed: Aug. 9, 2010

(65) Prior Publication Data

US 2011/0039278 A1 Feb. 17, 2011

Related U.S. Application Data

(60) Provisional application No. 61/232,033, filed on Aug. 7, 2009.

(51) Int. Cl.
*G01N 33/541* (2006.01)
*G01N 33/538* (2006.01)
*G01N 33/68* (2006.01)
*G01N 33/566* (2006.01)

(52) U.S. Cl.
USPC .......... 435/7.21; 422/69; 435/7.2; 435/287.2; 436/501

(58) Field of Classification Search
None
See application file for complete search history.

(56) References Cited

U.S. PATENT DOCUMENTS

| | | | |
|---|---|---|---|
| 4,981,785 A | 1/1991 | Nayak | |
| 5,358,691 A | 10/1994 | Clark et al. | |
| 5,599,677 A | 2/1997 | Dowell et al. | |
| 5,672,480 A | 9/1997 | Dowell et al. | |
| 5,885,530 A | 3/1999 | Babson et al. | |
| 6,159,750 A | 12/2000 | Edmonds | |
| 2004/0002168 A1 | 1/2004 | Remington et al. | |
| 2007/0003992 A1 | 1/2007 | Pentyala | |
| 2007/0196864 A1 | 8/2007 | Pentyala | |
| 2008/0227113 A1 | 9/2008 | Pentyala | |

FOREIGN PATENT DOCUMENTS

WO 9303367 A1 2/1993

OTHER PUBLICATIONS

International Search Report and Written Opinion; International Application No. PCT/US2010/044690; International Filing Date Aug. 6, 2010; Date of Mailing May 13, 2011; 12 pages.
Vawter, et al.; "Characterization of Human Cleaved N-Cam and Association with Schizophrenia"; Experimental Neurology; 172; pp. 29-46; (2001).
Yin, et al.; "Neuronal Pentraxin Receptor in Cerebrospinal Fluid as a Potential Biomarker for Neurodegenerative Diseases"; Brain Research; 1265; pp. 158-170; (2009).

*Primary Examiner* — Shafiqul Haq
*Assistant Examiner* — Galina Yakovleva
(74) *Attorney, Agent, or Firm* — Cantor Colburn LLP

(57) ABSTRACT

The present disclosure relates to detection of the presence or absence of cerebrospinal fluid (CSF) in a sample by the detection of one or more antigens that are enriched in CSF compared to their levels in other bodily fluids. The devices and methods are suitable for the detection of the presence or absence of cerebrospinal fluid in samples of mixed bodily fluids from a wide variety of human populations crossing ethnicity, age, gender, health status and genetic variability.

14 Claims, 9 Drawing Sheets

DEVICE AND METHODS FOR THE IMMUNOLOGICAL IDENTIFICATION OF CEREBROSPINAL FLUID

CROSS-REFERENCE TO RELATED APPLICATIONS

This application is a nonprovisional of U.S. Provisional Application No. 61/232,033 filed on Aug. 7, 2009, incorporated herein by reference in it entirety.

FIELD OF THE DISCLOSURE

The present disclosure relates to detection of the presence or absence of cerebrospinal fluid (CSF) in a sample by the detection of one or more proteins that are enriched in CSF compared to their levels in other bodily fluids. Described herein are devices and methods for the detection of the presence or absence of cerebrospinal fluid in samples of mixed bodily fluids from a wide variety of human populations crossing ethnicity, age, gender, health status and genetic variability.

BACKGROUND

Cerebrospinal fluid (CSF), or liquor cerebrospinalis, is found in the subarachnoid space as well as in the ventricles surrounding and penetrating the central nervous system (CNS). CSF bathes the brain and spinal cord and provides hydrative, nutritive, metabolic waste removal, and hydrostatic impact buffer to neurons and glia. CSF is produced from arterial blood by the choroid plexuses of the lateral and fourth ventricles by a combined process of diffusion, pinocytosis and active transfer. The fluid also contains constituents produced by neurons and glia. After diffusion through the ventricular system into the subarachnoid space, most of the CSF is reabsorbed by the arachnoid granulations to reenter the blood stream via the dural venous plexus. Approximately 500 ml of liquor is generated every day; with a total volume of 140-150 ml for an adult, the whole CSF is renewed every 6-8 hours. The CSF is bounded by the dura throughout the CNS. More fluid is produced in the rostral CNS and more ultimately drains in the caudal spinal cord to produce a net rostral to caudal fluid flow. CSF is an isotonic mixture mostly of salts, glucose, protein and water. CSF from the lumbar region contains 15 to 45 mg/dl protein (0.3-1% of serum protein concentration) and 50-80 mg/dl glucose (60% of blood glucose). Protein concentration in cisternal and ventricular CSF is lower.

The protein landscape of the CSF can be divided into two groups: Blood derived proteins, which make up the main fraction in the CSF of healthy individuals, and brain derived proteins. Approximately 20% of the proteins in the CSF originate from the brain parenchyma, but only a subset of those are actually brain specific.

Despite the fact that the majority of liquor proteins are also found in the serum, there are multiple sources for proteins unique to the CSF:

Proteins that are released from neurons and glial cells, e.g. tau protein, S-100, and neuron-specific enolase (NSE).

Proteins released from leptomeniges, e.g. β-trace protein and cystatin C.

Proteins differentially modified by glycosylation or phosphorylation during synthesis in the choroid plexus, e.g. transthyretin (TTR), angiotensin II, and Insulin-like growth factor II.

There is substantial overlap in the protein profile between CSF and plasma, a considerable number of proteins are unique to the CSF or are uniquely modified by phosphorylation or glycosylation in the CNS.

Lateral Flow Tests, or also known as Lateral Flow Immunochromatographic Assays or Strip Tests, are designed to rapidly detect the presence or absence of a given analyte in a heterogenous matrix. A variety of Lateral Flow Tests are currently on the market for home testing, point of care testing, or laboratory use, for instance pregnancy tests (e.g., FirstResponse®, ClearBlue®), HIV tests (e.g., OraQuick ADVANCE®, Clearview® Complete), or Chlamydia tests (e.g., Clearview® Chlamydia, InSTIcheck™ Chlamydia).

What is needed is a test suitable for detection of CSF that is comparable to HIV tests like OraQuick ADVANCE® or Clearview® Complete: It is a point of care test; the test is only qualitative; the operator needs minimal training to use the test; the test has an internal control on the strip to verify accurate sampling.

SUMMARY

In one embodiment, a device for detection of the presence or absence of cerebrospinal fluid in a sample comprises
a sample application region,
a sample labeling region comprising a first antibody to a CSF-enriched protein, wherein the first antibody is conjugated to a mobile particle;
a sample detection region comprising a second antibody to the CSF-enriched protein, wherein the second antibody is fixed to the sample detection region,
wherein the presence of a detectable band in the second region indicates the presence of cerebrospinal fluid in the sample.

In another embodiment, a method for detecting the presence or absence of CSF in a sample, comprises
contacting the sample with a binding partner specific for a CSF-enriched protein, and
detecting binding partner-CSF enriched protein complexes if present, wherein the presence of detectable complexes indicates the presence of CSF in the sample.

In the foregoing embodiments, the CSF antigen is Isoform 1 of Neural cell adhesion molecule-like (SEQ ID NO: 1; Accession Number gi:62088238) protein; Chain A, Human Mesotrypsin Complexed With Bovine Pancreatic Trypsin Inhibitor (Bpti) (SEQ ID NO:2; Accession number gi:162330095); CNTN2 Contactin-2 precursor (SEQ ID NO: 3; Accession Number gi|4827022); CNTN1 Isoform 2 of Contactin-1 (SEQ ID NO: 4; Accession Number gi:28373119); cDNA highly similar to SPARC-like protein 1 (un-named protein product) (SEQ ID NO: 5; Accession Number: gi|194388050); NRCAM protein (Neuronal cell adhesion molecule)[*Homo sapiens*] possibly slightly longer fragment (~96kDa) (Accession Number: SEQ ID NO: 6; gi|68534652 and SEQ ID NO: 7; gi|109731501); NCAM2 Neural cell adhesion molecule 2, isoform CRA_a (SEQ ID NO: 8; Accession Number gi|119630409); SERPINA3 serpin peptidase inhibitor, clade A, member 3 precursor/Isoform 1 of Alpha-1-antichymotrypsin/growth-inhibiting protein 25 [*Homo sapiens*] or slightly longer fragment of alpha-1-antichymotrypsin precursor (SEQ ID NO: 9; Accession Number gi|46981961); AGT Angiotensinogen (SEQ ID NO: 10; Accession Number gi|553181); Angiotensinogen precursor (Serpin A8) (SEQ ID NO: 11; Accession Number gi|4557287); unnamed protein product also called immunoglobulin superfamily, member 4B; in humans, also called cell adhesion molecule 3 (SEQ ID NO: 12; Accession Number gi|187608363); cDNA FLJ59893, dickkopf homolog 3 precursor (SEQ ID NO: 13; Accession Number gi|40548389); SERPINF1 serine (or cysteine) proteinase inhibitor, clade F (alpha-2 antiplasmin, pigment epithelium derived factor, Pedf), member 1 isoform 4 factor (SEQ ID NO: 14; Accession Number gi|15988024); human protein similar to GC Vitamin D-binding protein PREDICTED: vitamin D-binding protein [Pan troglodytes] (SEQ ID NO: 15; Accession Number 181482); CD14 Human monocyte antigen CD14 (CD14) (SEQ ID NO: 16; Accession Number gi|117646212); CADM3 Homo sapiens cell adhesion molecule 3 (CADM3), transcript variant 1 (SEQ ID NO: 17; Accession Number gi|90080503; SEQ ID NO: 18; gi|187608363 (human); Neural cell adhesion molecule variant (SEQ ID NO: 19; Accession Number gi:62088238); un-named protein similar to CLU cDNA FLJ57622, highly similar to Clusterin (SEQ ID NO: 20; Accession number gi|189054091); protein highly similar to Clusterin (SEQ ID NO: 21; Accession number gi|193787502); LMAN2 Vesicular integral-membrane protein VIP36 (SEQ ID NO: 22; Accession number gi|157834800); clusterin isoform 1 [Homo sapiens] (SEQ ID NO: 23; Accession number NM_001831.2); superoxide dismutase 3, extracellular precursor (SEQ ID NO: 24; Accession number gi|118582275); fibrin alpha C term fragment (SEQ ID NO: 25; Accession number gi|223057); Chain A, Human Kallikrein 6 (Hk6) Active Form or KLK6 Isoform 1 of Kallikrein-6 (SEQ ID NO: 26; Accession number gi|21465970); APCS Serum amyloid P-component/Chain A or Pentameric Human Serum Amyloid P Component (SEQ ID NO: 27; Accession number gi|576259); FAM3C Protein FAM3C/family with sequence similarity 3, member C precursor [Homo sapiens] note="predicted osteoblast protein; interleukin-like EMT inducer (SEQ ID NO: 28; Accession number gi|55629272); protein similar to unnamed protein product [Macaca fascicularis] also called immunoglobulin superfamily, member 4B; in humans, also called cell adhesion molecule 3 (SEQ ID NO: 29; Accession number gi|187608363); a CSF-enriched phosphorylated or dephosphorylated form of the foregoing CSF antigens; or a combination of two or more of the foregoing CSF antigens.

In another embodiment, a method for the detection of a reactant in a body fluid, tissue or microorganism comprises contacting the body fluid, tissue or microorganism with two or more antibodies, wherein each antibody specifically reacts with an antigen in the reactant, wherein reaction with each individual antibody does not indicate a positive test for the reactant, and wherein reaction with the two or more antibodies indicates a positive test for the reactant.

DETAILED DESCRIPTION

Figure 1:
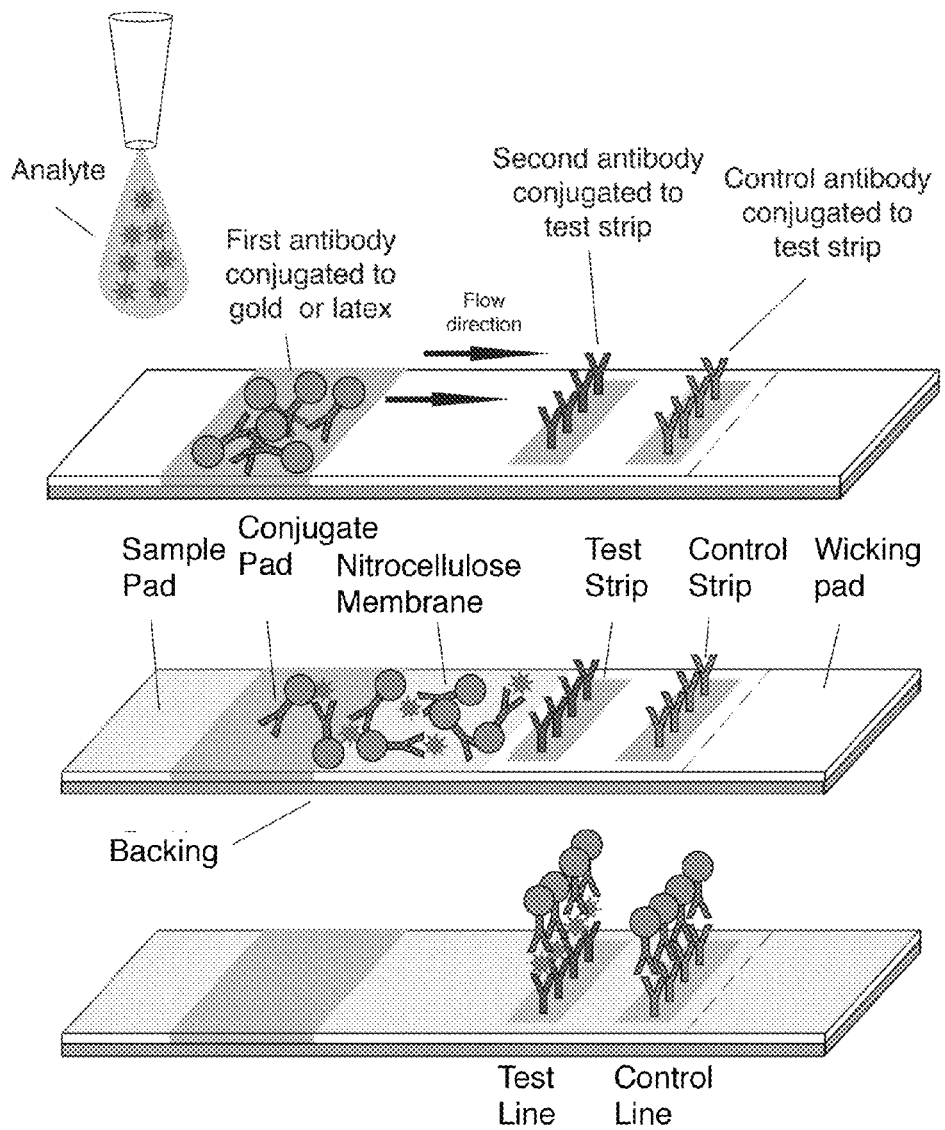
FIG. 1 Lateral Flow assay. Analyte is added to the left end of the strip either by a dropper or by direct dipping. The liquid (around 75 µl) is wicked across the strip to the right. The conjugate pad contains soluble IgG attached to a visible particle (i.e., gold or latex microspheres). If the analyte solution contains the analyte, the antibodies conjugate and the complex migrates across the strip. The mixture first encounters the test strip, which contains immobilized antibody against the analyte. The analyte, soluble primary and visible tag, then bind to the test line. If no analyte is present the soluble faction passes over the test line. Whether the analyte is present or not, excess soluble IgG bound to indicator binds to the immobilized anti-globin IgG bound to the control strip.

Described herein are proteins that are enriched in CSF compared to other bodily fluids and methods for the detection of the presence or absence of cerebrospinal fluid (CSF) in a sample by the detection of these proteins. Also described herein are devices and methods for the detection of the presence or absence of CSF in samples of mixed bodily fluids from a wide variety of human populations crossing ethnicity, age, gender, health status and genetic variability. The CSF-enriched proteins are detected with a specific protein binding partner such as an antibody, a ligand, a receptor, and the like. Binding partners can be natural or synthetic binding partners.

Binding can be detected either directly, or indirectly, such as with a fluorescent label attached to the binding partner. While several embodiments are included that use antibodies as binding partners, it should be understood that other binding partners can be used in place of antibodies.

In certain embodiments, the level of the CSF-enriched protein is quantitated. Such quantitation is particularly useful in the identification of brain injury. Quantitation can be performed by using a binding partner with a detectable label. "Detectable moiety" or a "label" refers to a composition detectable by spectroscopic, photochemical, biochemical, immunochemical, or chemical means. Useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available. The detectable moiety often generates a measurable signal, such as a radioactive, chromogenic, or fluorescent signal that can be used to quantitate the amount of bound detectable moiety in a sample. The detectable moiety can be incorporated in or attached to a binding partner either covalently, or through ionic, van der Waals or hydrogen bonds. The detectable moiety may be directly or indirectly detectable. Indirect detection can involve the binding of a second directly or indirectly detectable moiety to the detectable moiety.

In some embodiments, CSF detection is performed using a lateral flow assay, employing for example, antibodies specific for the CSF protein of interest. A lateral flow assay can be a single antigen assay or a multiple antigen assay. In one embodiment, a multiple antigen test uses all of the antigens together to provide a single easy to read answer (i.e., a single band on a strip assay). In another embodiment, a multiple antigen test qualifies or quantifies each of several antigens individually to give a more complex profile of the antigens that are present. Such a profile may be useful to determine the severity of a head injury, that is, the head injury is less severe when certain CSF-specific proteins are present and more severe when other CSF-specific proteins are present or levels of each protein provides a degree of injury Single Antigen Assay:

While lateral flow technology has been successfully used in many clinical assays, the unique and innovative approach described herein extends the technology to i.) bind single or multiple CSF-enriched proteins, thereby increasing sensitivity and specificity of the test, and/or ii.) detect a CSF-specific post-translational modification (e.g., phosphorylation).

As used herein, a CSF-enriched protein or CSF antigen or polypeptide is an antigen or polypeptide that is specific for CSF or substantially enriched in CSF compared to other bodily fluids. Table 1 identifies several proteins known to be concentrated in the CSF. These are not proteins identified in the current application, although they can, in some embodiments, be combined in an assay with one or more proteins identified herein in a multi-antigen assay.

TABLE 1

| Protein | MW (kDa) | CSF concentration | CSF/ serum ratio |
| --- | --- | --- | --- |
| β-trace protein | 25 | 16.6 mg/l | 34:1 |
| Cystatin C | 13.3 | 3.1 mg/l | 5:1 |
| Tau-protein | 55-74 | 0.2 µg/l | 10:1 |
| S-100 B | 21 | 1.5 µg/l | 18:1 |
| NSE | 78 | 8 mg/l | 1:1 |
| Transthyretin | 55 | 17 mg/l | 1:18 |
| Albumin | 67 | 245 mg/l | 1:205 |
| IgG | 150 | 25 mg/l | 1:440 |

Described herein are proteins that are present in sufficient quantities and enriched significantly in CSF compared to their levels in other bodily fluids, to act as a marker of CSF. The proteins found in pooled samples of CSF were compared to the proteins in blood, nasal fluid, saliva, sweat, tears and ear effluents (referred to as 'other bodily fluids'). CSF from a range of ages (1-70 years) and from both males and females was examined. Prior to comparative 2D gel electrophoresis, all fluids were treated to remove dominant serum proteins that are present in most bodily fluids (i.e., albumin, IgG, etc.). The remaining proteins from CSF and another bodily fluid were differentially tagged with Cy3 and Cy5 and run on two-dimensional PAGE. Using this approach, a novel set of proteins which are highly concentrated in the CSF over other bodily fluids were identified. CSF-enriched secondary modified proteins (i.e., phosphorylated) have also been identified. Dephosphorylation of CSF extracts confirmed that the CSF unique spots represent differential migration in the isoelectric dimension based on phosphorylation.

In one embodiment, the proteins that are enriched in CSF are used to detect CSF in an assay, such as a lateral flow assay. A lateral flow system consists of overlapping membranes containing the dried components needed for the test performance (FIG. 1). These membranes are assembled to small strips which can be placed into a plastic housing for better handling. The patient's material is loaded to the Sample Pad. In the case of whole blood/capillary blood samples a separation of blood cells and plasma takes place. The liquid fraction of the patient's sample diffuses through the Conjugate Pad containing labeled antibodies, which are specifically directed against the analyte of interest. The antibodies (conjugate) are re-dissolved and the analyte is specifically bound by the gold (or latex) conjugate. The analyte-gold-conjugate complex further diffuses through the Analytical Membrane. On this membrane two lines are arranged one after the other: (i) the Test Line containing a second set analyte-specific antibodies responsible for immobilizing the analyte-gold conjugate complexes and (ii) the Control Line fixing non-bound gold antibodies indicating that the conjugate has overflown the Test Line. If the analyte of interest is available above the detection limit the Test Line and the Control Line are clearly visible; if the analyte is below the detection limit only the Control Line appears during test time. The last component of the rapid test is the Wicking (or Sink) Pad which simply collects the fluid miming through the test system and preventing backflow of the fluid through the test system.

Lateral Flow Immunochromatographic Assays are designed either as sandwich assays or as competitive assays. Sandwich assays makes use of two different antibodies raised against the same analyte, one to color the analyte and one to concentrate the analyte at the test line. The test line will show as a colored band in positive samples. Competitive assays provide already colored analyte on the test strip and a set of antibodies against the analyte at the test line. The sample flows with the provided colored analyte towards the test line and competes for antibody binding. The test line will show as a colored band in negative samples.

CSF Assay Design Specifications:

The assay described herein can be used to accurately identify traces of CSF when it is mixed with a variety of non-CSF bodily fluids. These 'other fluids' are, for example, nasal and ear effluents, saliva, tears, sweat, urine and blood. The assay is intended to minimize false positive or false negative results regardless of the physiologic, metabolic or pathologic state, gender, age or ethnicity of the subject.

In one embodiment, the limit of detection is >5% CSF in a pure fluid or mixture of any of the above fluids. It may be possible to achieve a higher sensitivity but it will be essential to maintain the specificity in addition to the increased sensitivity. Thus, in some embodiments, a limit of detection of >1% CSF is achieved.

Multi Antigen CSF 'Tissue' Assay:

In one embodiment, the assay is one that will allow the detection of the presence of CSF via simultaneous detection of multiple CSF-enriched proteins. That is, the test includes two or more markers for CSF to provide improved reliability of CSF detection. Rather than testing for a single 'biomarker', the multiple marker assay will be robust and provide the correct answer under a variety of potential and unknown circumstances with high selectivity and sensitivity. For example, a single antigen assay may produce a false positive if the antibody recognizes an antigen in a fluid other than CSF (i.e. blood). If the assay tests for a antigen which is 'enriched' in CSF but not 'exclusive' to CSF, an aberrantly high blood level could produce a false positive. This may be problematic because it is not feasible to test the strip under all possible physiologic, pathologic, ethnic, sex, dietary, age-related, etc. conditions to look for false results. Further, the level of particular CSF antigen may be reduced below detection level, or a particular CSF antigen may have a rare genotypic difference, thus reducing reactivity in certain human populations thereby producing a false negative. These are all potential difficulties that arise from basing a test on a single CSF-enriched antigen (see FIG. 2). The novel 'Multi antigen' assay for detecting CSF in mixed body fluid samples should provide substantial improvement over single-antigen tests. In certain embodiments, the multi-antigen test includes at least one antibody specific for each of 2, 3, 4, 5, 6, 7, 8, 9 or 10 antigens that are enriched in CSF compared to their levels in other bodily fluids. In other embodiments, at least two antibodies specific for each antigen are employed.

Figure 2:
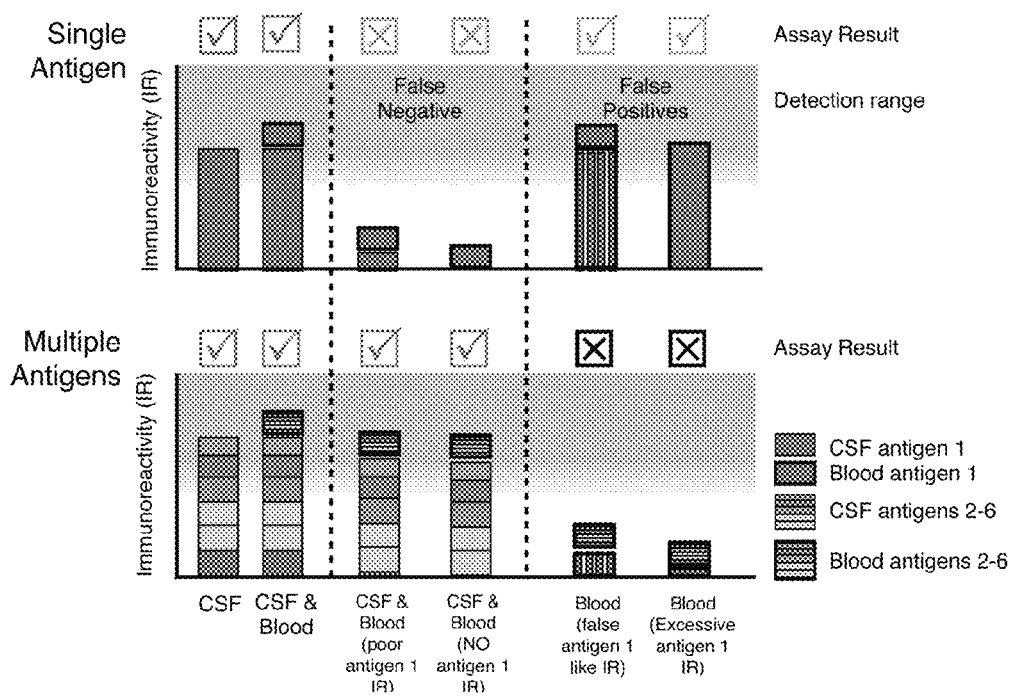
FIG. 2 shows advantages of a multi antigen approach to CSF detection. The upper figure represents single antigen assay results for various test conditions and the bottom figure shows results of the multi antigen assay. The bars along the X axis represent different assay conditions and the Y axis represents the degree of immunoreactivity seen by the assay. The upper shaded zone indicates a positive colorimetric response on the test line of the lateral flow assay. Assays with immunoreactivity that enters the shaded zone will produce a positive test result. Bar 1: CSF Bars in the upper graph illustrate immunoreactivity of the single antigen being sufficient to produce a positive test result. Alternatively in the multiple antigen graph (lower) a combination of antigens, each producing a partial signal accumulates to produce positive assay result. Bar 2: CSF contaminated with blood produces a similar positive response with a smaller but additive blood immunoreactivity (upper bar with thick border). Bar 3: Unusual CSF/blood sample in which antigen 1 is poorly immunoreactive. In the single antigen assay, the assay produces a false negative, while the multi antigen assay is still above assay threshold as a result of the other five antigen immunoreactivities being intact. Bar 4: CSF/blood with no antigen 1 immunoreactivity. Same results as in Bar 3. Bar 5: No CSF but blood borne cross-reactive antigen. In this case the single antigen assay produces a false positive, but as the immunoreactivity of the single antigen is not sufficient to produce a positive signal in the multi antigen assay the assay reports the correct negative result. Bar 6: No CSF but blood level of antigen 1 pathologically high. Single antigen assay produces false positive reacting to heightened blood levels. Multi antigen assay reacts to pathogentic antigen 1 levels in blood but does not reach threshold for false positive. This assay is shown with 5 antigen/antibody1/antibody2 mixes, however other embodiments could contain between 2 and as many as 10 antigen/antibody1/antibody2 mixes.
Figure 3:
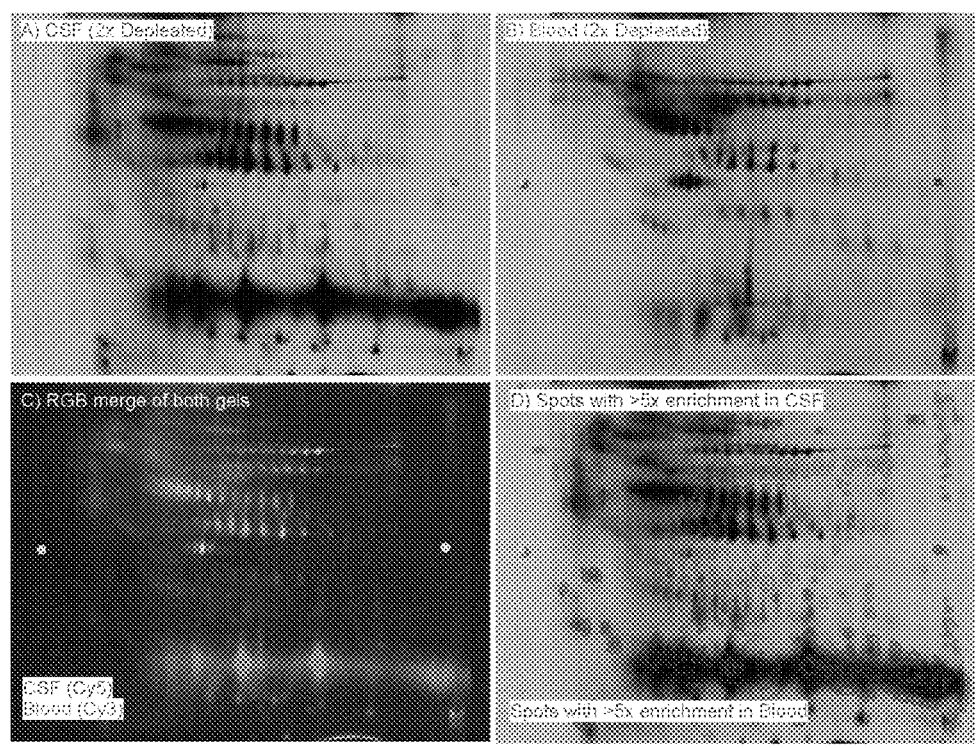
FIG. 3: Two dimensional gel electrophoresis of CSF and blood proteins. An example of a single experiment in which 100 µg of Cy-tagged CSF protein (A) and 100 µg of Cy3-tagged blood proteins (B) are separated in two dimensions. A and B are grayscale images of the same gel using different excitation and emission settings. The pH range is 4-8. C) is the RGB merge of the two channels with yellow spots indicating significant overlap. D) is an automated extraction of spots with >5× enrichment in either the CSF or blood. All samples were 2× depleted of major serum/CSF proteins (see Methods).
Figure 4:
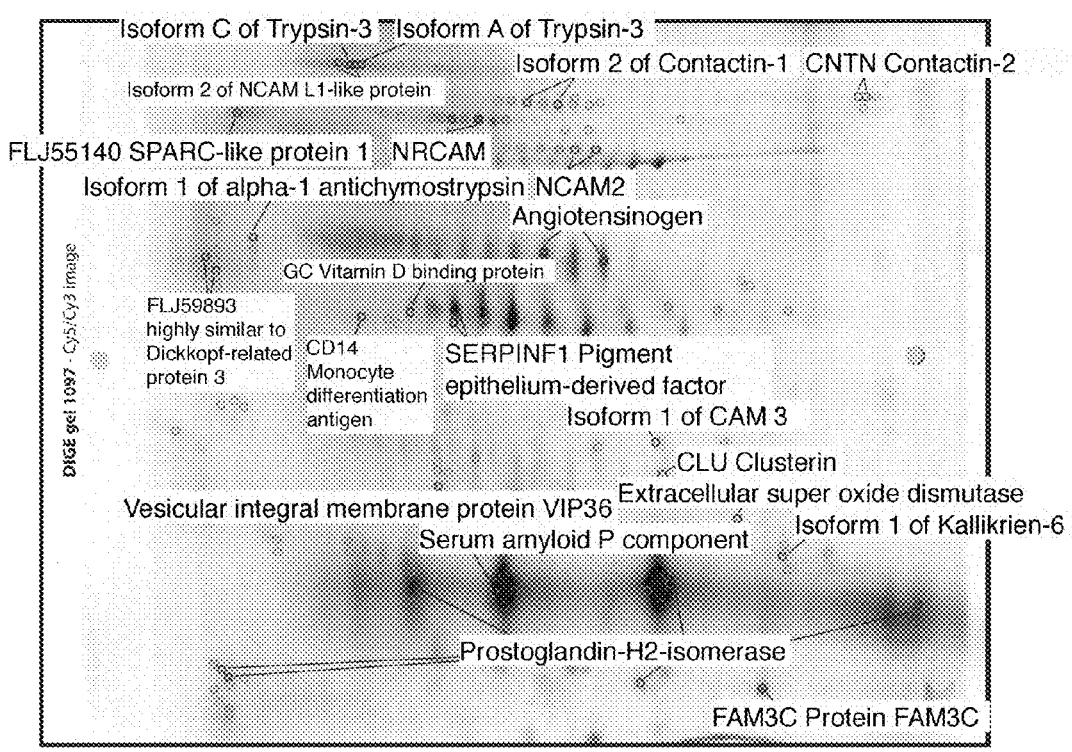
FIG. 4: Liquid chromatography-mass spectroscopy analysis of some of the CSF-enriched spots seen on the gel in FIG. 3.
Figure 5:
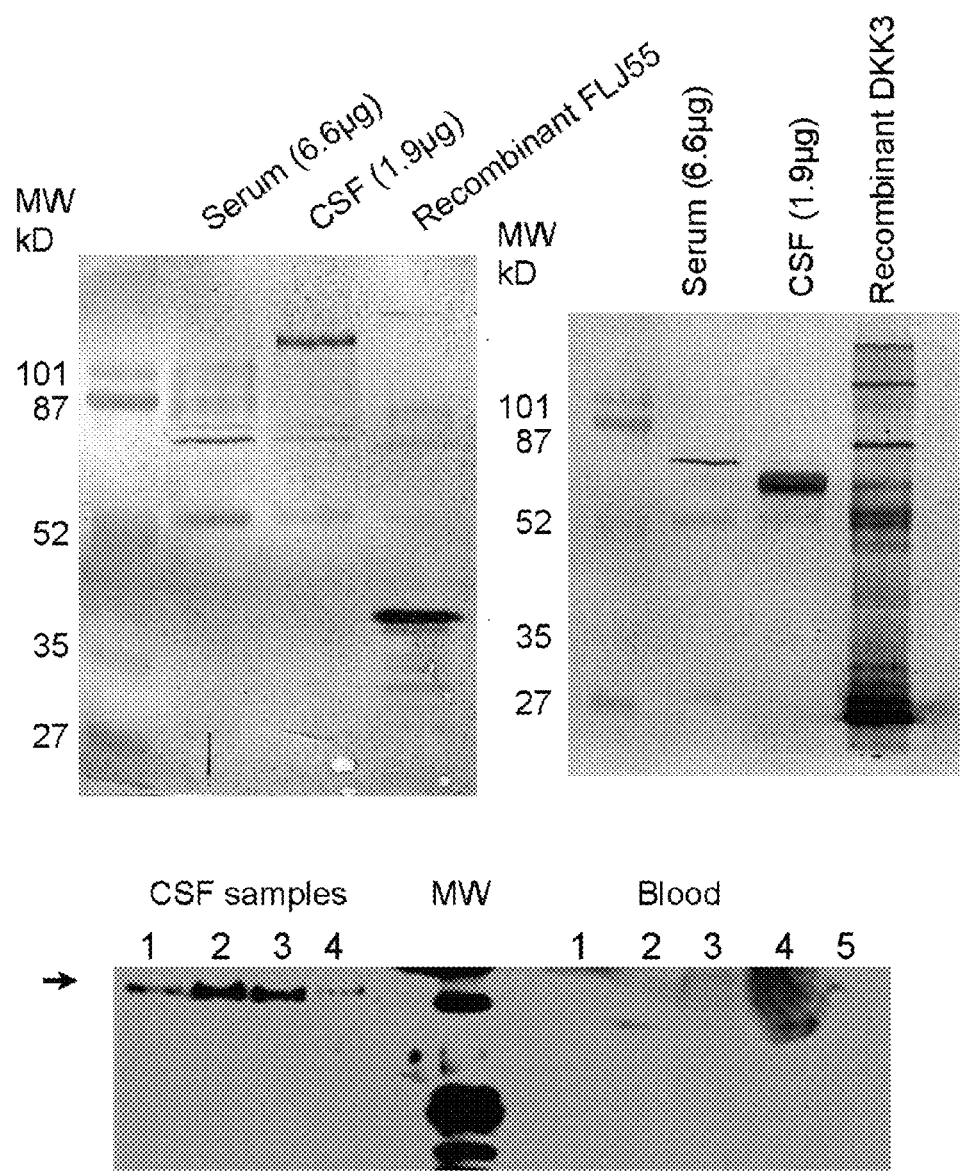
FIG. 5: CSF-enriched proteins FUSS and dickkopf homolog 3 precursor (DKK3). A) Immunoblot of FLJ55. Affinity purified polyclonal rabbit anti-human antibody produced against a recombinant fragment of FUSS produces immunoreactivity at the correct molecular weight in the CSF sample but not in the serum sample. B) Affinity purified polyclonal rabbit anti-human antibody produced against a recombinant fragment of DKK3 also produces immunoreactivity at the correct molecular weight in the CSF sample but not in the serum sample. In both cases excessive serum protein was loaded at levels higher then that of the sera. C) Four separate samples of CSF indicating immunoreactivity for DKK3 with a different affinity purified antibody (left). Five blood samples fail to produce immunoreactivity. Lane 5 blood is high non specific background.

As described herein, a large number of CSF-enriched protein spots have been extracted and analyzed by LC-MS. The rationale for this approach is illustrated in FIG. 2. Several CSF-enriched antigens have been identified and at least two different antibodies have been produced to each antigen. Mixtures of each of the two sets of IgG are added to the mobile and immobilized portions of the test strip (see FIG. 2), respectively. The multi antigen assay works by applying a concentration of antibodies for a particular antigen that are below the threshold for detection when all antibody molecules are bound. A mixture of several antibodies each a subthreshold levels are utilized in the assay. When CSF is added, all antibodies bind and accumulate producing a positive signal. The optimal embodiment would use at least 5-6 different antigens with a detection threshold of 4 so loss of a single antigen will not cause a false negative. In one embodiment, the device or test comprises 4 to 10 different antibodies that each specifically binds a different CSF antigens, wherein a positive test does not require binding to all antibodies. Accumulation of IgG/antigen on the test strip is linear and subthreshold levels for individual detection of each antibody are used then only the addition of other positive antibodies will produce a positive reaction. A positive response requiring accumulation of at least 4 IgG/antigens the assay will be more robust in the face of fluctuations in the levels of any one antigen. The assay will also be more robust in the face of aberrant increases in single antigen immunoreactivity in contaminating bodily fluids. Artifactual immunoreactivity of 1-3 of the antigens will not produce a positive test, therefore the test will be more robust and produce fewer false positives.

Identification of CSF-Enriched Proteins:

CSF samples from 1-40 individuals are pooled and 200 µl of the pooled samples are analyzed. Samples of sera from 1-40 individuals are pooled and 1 ml of pooled sera are analyzed. Major proteins shared by the blood and CSF (i.e. albumin, immunoglobins, etc.) were removed from both samples by repeated affinity chromatography.

In vitro label 50 µg of the control protein extract and 50 µg of the experimental protein extract with GE Healthcare Cy-3 and Cy-5 N-hydroxysuccinimidyl ester dyes. These dyes have been matched with respect to charge and mass—with the single positive charge of the dye replacing the charge lost by the modified lysine or N-terminus of the protein. Cy-3 and Cy-5 labeled proteins co-migrate—with the dye label adding approximately 450 Da to the proteins in each sample.

Control, experimental, and internal standard samples were mixed together (i.e., 150 µg total protein) and then an equal volume of 2× Sample Buffer added.

The volume was brought up to 450 ul with Rehydration Buffer Immobiline™ (IPG) Drystrips (GE Healthcare) 24 cm were rehydrated for 10-24 hrs, and isoelectric focusing carried out. We used a number of different pH ranges including: 3-7, 4-7, 3.5-4.5, 4.0-5.0, 4.5-5.5, 5.0-6.0, 5.5-6.7, and 6-9. SDS polyacrylamide gel electrophoresis (second) dimension was carried out on a 10 inch wide by 7.5 inch tall by 1.0 mm thick gel with one side coated with Gelbond®. We used a 12.5% polyacrylamide gel which will optimally separate 12-100 kD proteins.

Immediately after SDS PAGE, the gel (which is still held between two glass plates) was scanned at all 3 wavelengths simultaneously on the GE Healthcare Typhoon™ 9410 Imager. After scanning, 16 bit TIFF files of each color channel were exported for image analysis using the differential in-gel analysis module of the GE Healthcare DeCyder software package. After spot detection (which includes automatic background correction, spot volume normalization and volume ratio calculation), a user defined "dust filter" was applied to each gel. This has the effect of automatically removing non-protein spot features from the gel and is followed by recalculation of experimental parameters.

The front glass plate was removed and the gel was then fixed and stained with Sypro Ruby, which is the fluorescent stain that was used as a guide to excise spots of interest from the gel. The reason for using Spyro Ruby, which stains all protein in the gel, is that the Cy-dye labeling is carried out such that the extent of incorporation will be <5% in terms of mole Cy-dye/mole protein. Since the Cy-dye has a MW of about 580 Da, low MW proteins (e.g., 10 Kd) labeled with Cy-dyes will not exactly co-migrate in the SDS PAGE dimension with their non-labeled counterparts.

GE Healthcare DeCyder™ software was used to quantify the gel image and to identify a "pick list" of differentially expressed protein spots to be excised and subjected to MS-based protein identification. The DeCyder™ software can analyze any two Cy-dyed gel images, either on the same gel or on different gels, match the spots between the two images, and then identify differentially expressed protein spots. The DeCyder™ software automatically outputs a listing of statistically significant differences in protein expression including t-test values, using the Cy-2 internal standard. Differentially expressed spots were identified using a number of criteria including area, volume, 3D peak slope, 3D peak height, and/or statistical variation. Protein spots that show different degrees of intensity between the two samples were highlighted by the software and confirmed manually. The DeCyder™ software was also used to analyze Sypro Ruby images, match the spots found with Sypro staining to those identified with the Cy-dye stains, and then choose a 'pick list' from the Sypro stained gel image.

The protein spot pick list was transferred to the Ettan™ Spot Picker instrument (GE Healthcare) which automatically excised the selected protein spots from the gel and transferred them into a 96-well microtiter plate.

The excised protein spots were then subjected to automated in-gel tryptic digestion on the Ettan™ TA Digester.

An aliquot of each digest was spotted (along with matrix) onto a MALDI-MS target.

High mass accuracy, automated MALDI-MS/MS spectra were acquired on each target (using an Applied Biosystems 4800 Tof/Tof instrument) and the resulting peptide masses were subjected to database searching using Mascot algorithms.

The remaining aliquots of digests of protein spots that are not identified by this approach were subjected to nanospray or LC/MS/MS analysis (Micromass Q-Tof) with the resulting MS/MS spectra then being subjected to Sequest database searches to identify proteins present in the sample.

Figure 6:
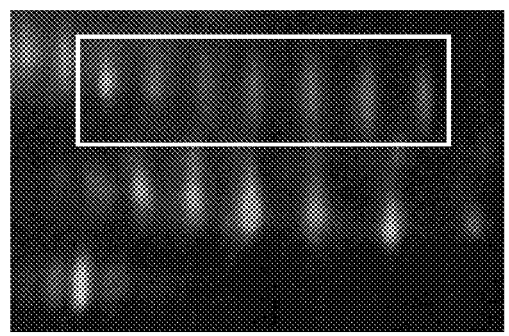
FIG. 6: Phosphorylated forms of angiotensinogen that are highly enriched in the CSF. An RGB merge of the Cy3 blood (green) and Cy5 CSF (red). We have identified several novel and non-overlapping phosphorylated versions (right four red spots) that are not present in the blood. At least three other combinations (left three spots) are present in both CSF and blood.
Figure 7:
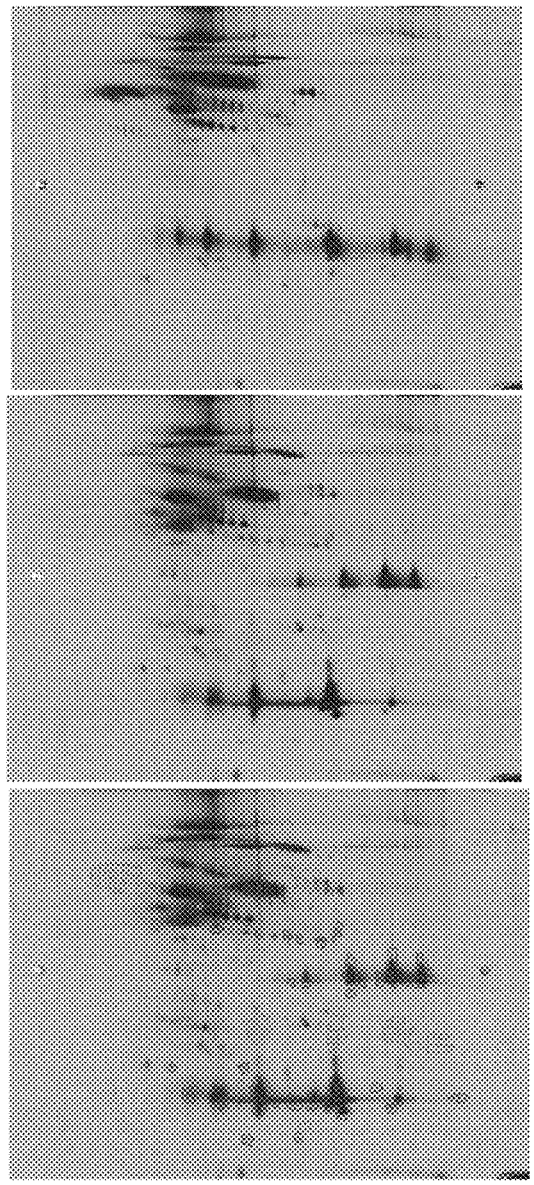
FIG. 7: CSF specific post translational modifications. Change in the CSF 2D gel protein distribution pattern before (top panel) and after (middle panel) removal of all secondary modifications of the extracted proteins. Red spots in lower panel indicate a reduction in a particular protein signal following removal of the post-translational modification.
Figure 8:
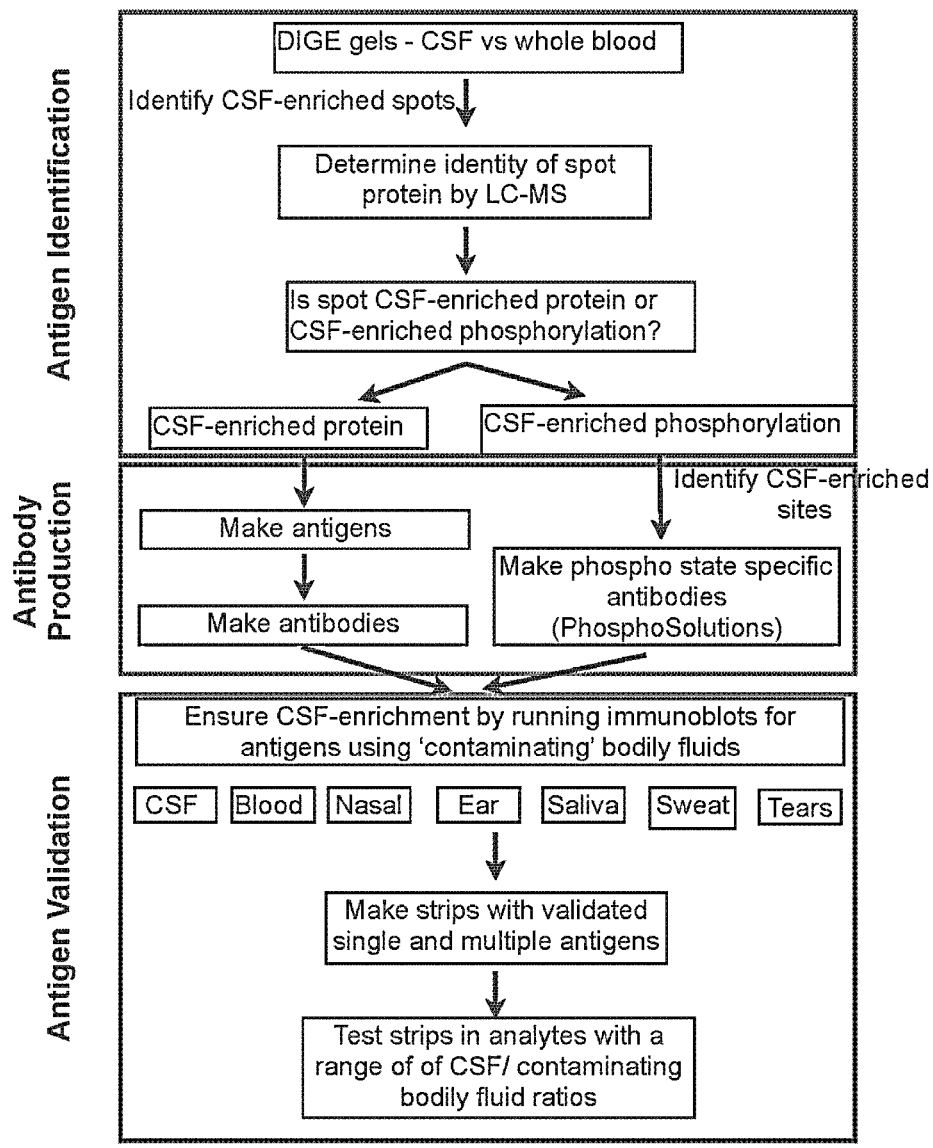
FIG. 8: Experimental flow chart for the production of CSF detection test strips.
Figure 9:
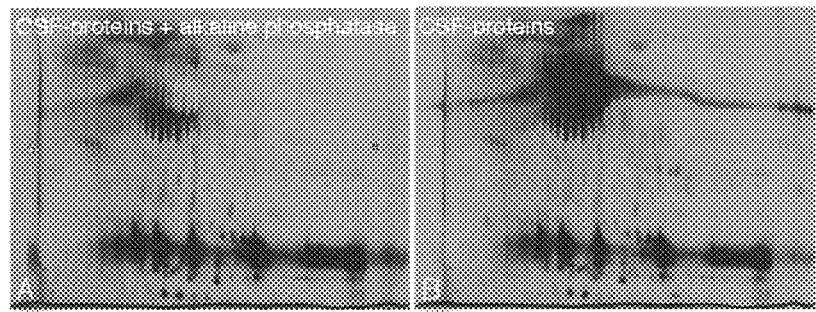
FIG. 9: CSF proteins that are phosphorylated. A single DIGE gel in which two samples of serum protein depleted CSF was run. A) the Cy3 labeled proteins from the CSF sample which was incubated in alkaline phosphatase for one hour. B) Equivalent sample of serum protein depleted CSF not treated with alkaline phosphatase. C) Computer generated difference (blue boundaries) between spot volume of the two gels (A vs B). All blue spots represent phosphorylated CSF proteins.

CSF-Enriched Protein Phosphorylation Sites as Antigens for a CSF Test Strip:

During the course of Fluorescence Difference Gel Electrophoresis (DIGE) experiments to identify CSF-enriched proteins, spots distributed in the pH dimension that were highly CSF-enriched (i.e. not present in blood samples) were identified, however upon protein identification by LC-MS, it was established that many of these proteins were in fact present in the blood but had a different patterns in the pH dimension of the gel (FIG. 6). Regularly spaced spots of the same molecular weight often represent differentially phosphorylated versions of the same protein. The differential and regular migration in the pH dimension is indicative of the large but quantal nature of the negative charge on the $PO_3^-$ groups. Upon phosphopeptide mapping of these spot arrays, it was determined that this was in fact the case. Several of these proteins (including angiotensinogen, (FIG. 6) had highly CSF-enriched phosphorylations. In some cases these phosphorylation sites were serine/threonine phosphorylations, and in other cases they were tyrosine phosphorylations. In all, proteins were selected with multiple CSF-enriched sites per protein (i.e. angiotensinogen). As it is possible to produce antibodies that recognize a single epitope only when phosphorylated, phosphorylation sites will be included as antigens in the assays described herein. These phosphorylated epitopes are attractive as candidates as they are very prevalent and the presence of two CSF-enriched phosphorylation sites on a single protein opens the door to making pairs of antibodies to different sites that can be used differentially on the mobile and immobile regions of the strip to require dual phosphorylation for a positive response. We have run DIGE gels comparing CSF proteins that have been dephosphorylated with alkaline phosphatase (FIG. 9). This has identified proteins listed herein as differentially phosphorylated in the CSF.

Identification of antigens is performed using 2 dimensional DIGE gel electrophoresis followed by trypsin digestion and LC-MS. The dominant proteins in both blood and CSF are removed by affinity columns prior to electrophoresis. These proteins are ubiquitously present in bodily fluids (i.e. albumin, immunoglobins etc.). We run all samples doubly across columns to remove 14 dominate serum proteins. We run the extracted proteins from 1-2 mls of whole blood on gels along with proteins from 200 µl of CSF. This enriched the blood proteins to ensure we are identifying proteins that are enriched in the CSF. Proteins from the CSF are labeled using either Cy3 or Cy5 fluorophores. In contrast blood proteins are labeled with either Cy5 or Cy3, respectively. The samples are then mixed and loaded on a 2 dimensional PAGE gel. Numerous different gels are run focusing on different regions of the molecular mass dimension (Y-dimension) and pH dimension (X-dimension). Following running of the gel, the intensity of the differentially visualized fluorescently labeled proteins are quantified and compared by an automated computer program. Those spots that are enriched by at least 5× in the CSF are robotically collected, trypsin digested and analyzed by LC-MS. Peptide molecular weights are compared to published databases. Enriched proteins are selected as candidates and standard molecular biologic methodology are employed for the production of Histidine-tagged recombinant proteins in bacteria or alternatively peptides corresponding to specific regions of the proteins are produced synthetically. Monoclonal and polyclonal antibodies are produced by a commercial house using provided antigens. Affinity purification is performed by standard column techniques utilizing cyanogen bromide-activated columns and recombinant proteins used for immunization. CSF-specific antigens are identified by trypsin and chymotrypsin digestion followed by LC-MS and phosphopeptide determination.

Validation of CSF-enriched antibodies is conducted by separating discrete volumes of whole bodily fluid proteins on SDS-PAGE, transferring to nitrocellulose membranes, immunoblotting first with primary antibodies against the antigens and then HRP-labeled secondary antibodies followed by ECL quantification. Antigens that have a >5× immunoreactivity in CSF over levels larger volumes of whole blood, nasal and ear effluents, tear, saliva or sweat are pursued. Samples of bodily fluids from 20 to 30 different individuals of each are tested for each antigen. Fluid samples are purchased from commercial laboratories that assure purity or directly collected. Bodily fluids are tested from individuals ranging in age from infants to elderly (75 years), male and female, as well as several common pathological conditions (i.e. advanced stage diabetes, coronary artery disease, asthma, etc.).

To identify phosphorylation state specific antigens, two-dimensional gels are produced as described above however three labeled protein fractions are produced (Cy2, Cy3 and Cy5): CSF, whole blood and CSF proteins in which all protein phosphorylations have been removed by alkaline phosphatase in an additional step prior to labeling. A comparison is then made between the dephosphorylated and normal CSF channels for alterations. Spots that disappear following dephosphorylation and are not present in the blood protein fluorescence channel are collected and sequenced. Absolute identification of the site of phosphorylation is determined by phospho peptide and phospho amino acid analysis, in vitro phosphorylation of recombinant proteins and protein fragments and immunoreactivity with phosphostate specific antibodies.

Once antibodies have been selected for use in the test strips, the relative affinity of each of the antibodies will be determined by running dilution curves using pure samples of recombinant antigens. This will guide the mixing of antibodies for inclusion on test strips.

In one embodiment, included herein are devices and methods for rapid, bedside or triage site testing of bodily fluids, surgical sites or wounds for the presence of cerebrospinal fluid. In another embodiment a test is proposed that allows detection of CSF enriched proteins in samples of blood, plasma or sera as an indication of central nervous system (CNS) injury, breach or damage. Tests can include a single or multiples of the antigens described herein as markers of damage to the CNS. Described herein are newly-identified CSF-specific or enriched antigens that can be used individually or in combination to detect CSF in a broad spectrum of individuals from pediatric to geriatric, and despite the presence of diseases, personal habits, or individual genetic variability that might alter the composition of bodily fluids.

In one embodiment, included herein are devices for the detection of cerebrospinal fluid in samples such as those suspected of containing cerebrospinal fluid, wherein the devices include one or more antibodies specific for one or more CSF antigens as described above. The CSF antigens can be employed in combinations to enhance the signal to noise ratio and to overcome individual variability in the expression of the antigens described above in different bodily fluids. In some embodiments, the detection of multiple antigens provides superior sensitivity and selectivity over detection of a single CSF-enriched antigen.

In one embodiment, described herein are devices for the detection of cerebrospinal fluid in samples such as those suspected of containing cerebrospinal fluid, wherein the devices include one or more antibodies specific for one or more CSF antigens in a state of post-translational modification that is specific to the cerebrospinal fluid and distinguishable from the same antigen in other bodily fluids by virtue of the post-translational modification.

In some embodiments, described herein are devices for the detection of cerebrospinal fluid in samples such as those suspected of containing cerebrospinal fluid, wherein the devices include one or more antibodies specific for one or more CSF antigens in a state of phosphorylation that is specific to the cerebrospinal fluid and distinguishable from the same antigen in other bodily fluids by virtue of the phosphorylation.

Samples for testing using the devices disclosed herein can be taken from different sites in the human body, such as at a site of surgery (i.e. head, neck, ear, throat, nasal or spinal surgeries) where the potential for CSF leakage is possible; at a site of epidural injection or spinal tap; or at a site of wounds in areas where a breach of the meninges is possible (i.e. head, neck, spinal cord, nasal compartment, nose, ears, throat, skull, etc.), or where the injured party demonstrates signs of possible meningeal breach or serious injury to the central nervous system; or at a site of epidural injection, spinal injection or spinal tap. The antigens identified herein are particularly good markers for brain injury. Additional samples include saliva and urine samples.

The unique approach of performing 2D-DIGE studies to compare the components of human CSF and serum has yielded a number of antigens that are specific to, or highly enriched in CSF. Antibodies specific for these antigens are markers of the presence of CSF in bodily fluids, or at wound, surgical or injections sites where its presence would be atypical and potentially threaten the health or life of a patient or trauma victim.

In some embodiments, the above-described CSF antigens have post-translational modifications such as phoshorylation, glycosylation, sumoylation, ubiquitination, lipidation, nitrosylation, acetylation, neddylation, where those post-translational modification are specific to the CSF form of the antigen may be used by the lateral flow assay, western blots, ELISA or immunoprecipitation.

In some embodiments, multiple antigens may be used and may include combinations of antibodies that detect simple antigens (i.e., unmodified antigens) with antibodies that detect post-translationally modified antigens such as described above and in any of the various assays, lateral flow, Western blot, ELISA, or immunoprecipitation.

In one embodiment, antibodies are used to determine if a sample contains polypeptides associated with the presence of CSF indicating the presence or absence of CSF. Antibody binding is detected by, for example, radioimmunoassay, ELISA (enzyme-linked immunosorbant assay), "sandwich" immunoassays, immunoradiometric assays, surface plasmon resonance, immunocytochemistry, immunohistochemistry, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, and the like. Detection of antibody binding can be achieved using enzymatic, colorimetric, fluorescent, bioluminescent, luminescent, colored latex beads, colloidal gold and/or silver methods.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a score correlating to the presence of specific polypeptides and likelihood of CSF in a sample based on the result of the immunoassay is utilized.

In other embodiments, the immunoassay is as described in U.S. Pat. Nos. 5,599,677 and 5,672,480, each of which is herein incorporated by reference.

Provided herein are isolated antibodies or antibody fragments (e.g., Fab fragments, $Fab_2$ fragments, and the like). Antibodies can be generated to allow for the detection of polypeptides associated with the presence of CSF. The antibodies are prepared using various polypeptides, synthetic peptides and/or recombinant proteins associated with the presence of CSF and fragments thereof In one embodiment, the immunogens are polypeptides, synthetic peptides and/or recombinant proteins associated with the presence of CSF to generate antibodies that recognize the polypeptides associated with the presence of CSF. In one embodiment, the antibody is reactive with a native or "folded" protein. In another embodiment, an antibody is reactive with denatured protein (including detergent solubilized). Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein or peptide as the antigen according to a conventional antibody or antiserum preparation process.

Various procedures are used for the production of polyclonal antibodies directed against polypeptides associated with the presence of CSF. For the production of an antibody, various host animals are immunized by injection with the polypeptides, synthetic peptides and/or recombinant proteins associated with the presence of CSF or a fragment thereof including but not limited to rabbits, mice, rats, sheep, goats, chicken, donkey, etc. In a specific embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward polypeptides, synthetic peptides and recombinant proteins associated with the presence of CSF, it is contemplated that a technique that provides for the production of antibody molecules by continuous cell lines in culture will find use herein. These include, but are not limited to, the hybridoma technique originally developed by Kohler and Milstein, as well as the trioma technique, the human B-cell hybridoma technique, and the EBV-hybridoma technique to produce human monoclonal antibodies.

In additional embodiments, monoclonal antibodies are produced in germ-free animals. Furthermore, it is contemplated that human antibodies will be generated by human hybridomas or by transforming human B cells with EBV virus in vitro.

In addition, it is contemplated that techniques described for the production of single chain antibodies will find use in producing single chain antibodies. An additional embodiment utilizes the techniques described for the construction of Fab expression libraries to allow rapid and easy identification of monoclonal Fab fragments with the desired specificity.

In other embodiments, contemplated are recombinant antibodies or fragments thereof to polypeptides associated with the presence of CSF. Recombinant antibodies include, but are not limited to, humanized and chimeric antibodies. Methods for generating recombinant antibodies are known in the art.

It is contemplated that a technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. The immunogenic peptide may be provided free of the carrier molecule used in any immunization protocol. For example, if the peptide was conjugated to KLH, it may be conjugated to BSA, or used directly, in a screening assay.

The foregoing antibodies can be used in methods known in the art relating to the localization and structure of polypeptides associated with the presence of CSF (e.g., for Western blotting), measuring levels thereof in appropriate biological samples, etc. The antibodies can be used to detect polypeptides associated with the presence of CSF in a biological sample from an individual. The biological sample is a biological fluid, such as, but not limited to, tissue, blood, serum, plasma, urine, nasal and ear effluents, saliva, sweat, tears and the like. In one embodiment, the sample is from an individual suspected of having a brain injury, such as mild traumatic head injury received during participation in sporting events, auto accidents, military activity and motorcycle accidents. The test would be most useful when the injury is mild to moderate in severity. More severe head injury including penetrating injuries generally already receive the necessary level of medical attention. Diagnosis of traumatic brain injuries generally requires a short neurological exam (the GCS). The precise designations of mild and moderate are sometimes hard to objectively identify without a recent baseline, pre injury test. Other injuries or treatments (sedative, anesthetics, etc) can interfere with the test. The current set of antigens can represent "biomarkers" which could be used to "fingerprint" the existence and severity of a head injury. A rapid test that is qualitative or quantitative of the existence of a subset of these antigens in blood or other bodily fluids (sweat, urine, saliva, etc.) can be used as a measure of the severity of an injury in combination with a GCS or any such neurological exam. Often the severity of a mild to moderate head injury is not know and to what degree the person should continue to engage in critical activities (i.e. continuing to participate in a sporting event, continue to work or drive a vehicle, remain in the combat arena, continue to assume a command position in combat, operate heavy machinery, etc.). A more objective test of blood borne or secreted proteins normally found enriched only in the CSF would represent a diagnostic test of injury.

The biological samples can then be tested directly for the presence of polypeptides associated with the presence of CSF using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS) Triton, Non-iodet (or other ionic or non-ionic detergents), and the presence of a CSF antigen detected by immunoblotting (Western blotting). Immunoblotting techniques are generally more effective with antibodies generated against a peptide corresponding to an epitope of a protein, and hence, are particularly suited to the present disclosure.

The correlation step mentioned above may be implemented qualitatively or quantitatively, for example in a fluorophoric or colorimetric assay.

Kits and Devices:

Also provided are kits and devices for determining whether a sample contains polypeptides associated with the presence of CSF. The diagnostic kits and devices are produced in a variety of ways. In some embodiments, the kits and devices contain at least one reagent for specifically detecting a polypeptide associated with the presence of CSF. In specific embodiments, the kits and devices contain multiple reagents for detecting polypeptides associated with the presence of CSF. In other embodiments, the reagents are antibodies that preferentially bind polypeptides associated with the presence of CSF. The test can produce a single result indicating the presence of CSF from a number (2-10) of tests for multiple antigens or each test can produce a different evident result that can be interpreted to indicate the presence or absence of CSF.

In some embodiments, the kit or device contains instructions for determining whether the sample contains polypeptides associated with the presence of CSF. In specific embodiments, the instructions specify that presence or absence of CSF is determined by detecting the presence or absence of polypeptides associated with the presence of CSF in a sample from the subject.

In some embodiments, the kits and devices include ancillary reagents such as buffering agents, protein stabilizing reagents, and signal producing systems (e.g., fluorescence generating systems such as FRET systems). The test kit or device is packaged in a suitable manner, typically with the elements in a single container or various containers as necessary, along with a sheet of instructions for carrying out the test. In some embodiments, the kits or devices also include a positive control sample. In further embodiments, the kit or device contains comparative reference material to interpret the presence or absence of polypeptides associated with the presence of CSF according to intensity, color spectrum, or other physical attribute of an indicator.

The need for a rapid, reproducible, sensitive and simple diagnostic test, which can be used in the health care for diagnosing CSF, is of major importance. Such a test has the obvious advantage over the existing laboratory tests, i.e., immunofixation electrophoresis, enzyme-linked immunosorbant assay (ELISA) and immunoblotting, in that it can be performed immediately beside the patient giving a result in a few minutes of time instead of several days when the sample is sent for analysis to a laboratory. A lateral flow immunochromatographic test may be utilized for making a diagnostic kit for the detection of CSF in biological fluids.

In one embodiment, a device includes a solid phase comprising a first region comprising a mobile indicator suitable for binding a CSF antigen, and a second region comprising a fixed indicator suitable for binding the CSF antigen.

In one embodiment, a lateral flow device comprises a test strip optionally with a plastic test cassette. Antibodies are attached to three different zones on the membrane; a sample zone (S) containing a first monoclonal antibody to a polypeptide associated with the presence of CSF; a test zone (T) that contains a second monoclonal or polyclonal antibody to polypeptides associated with the presence of CSF immobilized to the membrane; and a control zone (C), which contains a control antibody, for example, an immobilized rabbit anti-mouse antibody. The first monoclonal antibody in the sample (S) zone may be conjugated to a mobile particle, for example, a colored latex particle or a gold particle. Alternatively, the first monoclonal antibody is conjugated to a chromophoric indicator, such as a fluorescent molecule or tag (Green Fluorescent Protein (GFP) or FP orthologs mutants and other naturally occurring GFP-like fluorescent and chromo proteins, fluorescein (and orthologs), rhodamine (and orthologs), Cy3, Cy5, Cy2, Cy7, Cy8, Alexa® dyes, Texas Red, and the like).

An exemplary device is implemented utilizing an immunochromatographic test based on the use of two monoclonal antibodies. Sample is added to the S-zone, and if the polypeptide associated with the presence of CSF is present, it binds to the first monoclonal antibody to form a polypeptide-conjugate-complex. This complex migrates chromatographically on the membrane, and when it reaches the immobilized antibody in the T-zone, agglutination takes place and a blue colored band is formed.

Briefly and in one embodiment, the first monoclonal antibody is conjugated to a mobile particle, for example, gold or latex beads. These beads have the intrinsic color of either being red (for gold) or can come in different colors if using latex beads. When the sample is applied on the "S-zone", the marker, a polypeptides associated with the presence of CSF if present in the sample, binds to the first monoclonal antibody that is conjugated to the beads and then because of the lateral flow absorbent pad on which the beads are placed, the complex (beads+antibody+polypeptide if present in the sample) migrates laterally. Once the complex reaches the "T-zone" where the second antibody is immobilized on the strip, the marker that is now migrating with the complex binds to the second immobilized antibody. As the second antibody is stationary/fixed/immobilized, the whole complex gets trapped and as the complex now contains colored beads, the immobilized T-zone line lights up according to the beads that are used (red for gold or different colors {like blue} if latex beads are used). The excess complex sample migrates to the end of the strip and at the "C-zone" the first antibody conjugated to the beads is trapped by immobilized/fixed/stationary rabbit-anti mouse antibody and gives a colored line indicating that the test is complete). Thus, a colored band indicates a positive result. No band in the T-zone is significant for a negative result. The immobilized polyclonal antibody in the C-zone will bind the latex conjugate with both positive and negative samples. This blue band assures a correct test performance.

In practice, the kits and devices are utilized in a variety of clinical settings to determine the presence of CSF in a sample.

The invention is illustrated by the following non-limiting examples.

EXAMPLES

CSF-specific antigens newly identified herein include Isoform 1 of Neural cell adhesion molecule-like (Accession Number gi|62088238) protein; Chain A, Human Mesotrypsin Complexed With Bovine Pancreatic Trypsin Inhibitor (Bpti) (Accession number gi|162330095); CNTN2 Contactin-2 (Accession Number gi|4827022); CNTN1 Isoform 2 of Contactin-1 (Accession Number gi:28373119); cDNA highly similar to SPARC-like protein 1 (Accession Number: gi|194388050); NRCAM protein (Neuronal cell adhesion molecule)[*Homo sapiens*] possibly slightly longer fragment (~96kDa) (Accession Number: gi|68534652 and gi|109731501); NCAM2 Neural cell adhesion molecule 2 (Accession Number gi|119630409); SERPINA3 serpin peptidase inhibitor, clade A, member 3 precursor/Isoform 1 of Alpha-1-antichymotrypsin/growth-inhibiting protein 25

[Homo sapiens] or slightly longer fragment of alpha-1-antichymotrypsin precursor (Accession Number gi|46981961); AGT Angiotensinogen (Accession Number gi|553181); Angiotensinogen precursor (Serpin A8) (Accession Number gi|4557287); unnamed protein product also called immunoglobulin superfamily, member 4B; in humans, also called cell adhesion molecule 3; possible fragment (Accession Number gi|187608363); cDNA FLJ59893, dickkopf homolog 3 precursor (Accession Number gi|40548389); SERPINF1 serine (or cysteine) proteinase inhibitor, clade F (alpha-2 antiplasmin, pigment epithelium derived factor), member 1 isoform 4 [Pan troglodytes] factor (Accession Number gi|15988024); GC Vitamin D-binding protein PREDICTED: vitamin D-binding protein [Pan troglodytes] (Accession Number 181482); CD14 Human monocyte antigen CD14 (CD14) (Accession Number gi|117646212); CADM3 *Homo sapiens* cell adhesion molecule 3 (CADM3), transcript variant 1 (Accession Number gi|90080503; gi|187608363 (human); Neural cell adhesion molecule variant (Accession Number gi|62088238); CLU cDNA FLJ57622, highly similar to Clusterin (Accession number gi|189054091); protein highly similar to Clusterin (Accession number gi|193787502); LMAN2 Vesicular integral-membrane protein VIP36 (Accession number gi|157834800); superoxide dismutase 3, extracellular precursor (Accession number gi|118582275); fibrin alpha C term fragment (Accession number gi|223057); KLK6 Isoform 1 of Kallikrein-6 (Accession number gi|21465970); APCS Serum amyloid P-component/Chain A, The Structure Of Pentameric Human Serum Amyloid P Component (Accession number gi|576259); FAM3C Protein FAM3C/family with sequence similarity 3, member C precursor [*Homo sapiens*] note="predicted osteoblast protein; interleukin-like EMT inducer (Accession number gi|55629272); Chain A, Human Kallikrein 6 (Hk6) Active Form With Benzamidine Inhibitor (Accession number gi|21465970); unnamed protein product [*Macaca fascicularis*] also called immunoglobulin superfamily, member 4B; in humans, also called cell adhesion molecule 3; possible fragment (Accession number gi|187608363); a CSF-enriched phosphorylated or dephosphorylated form of the foregoing CSF antigens; or a combination of two or more of the foregoing CSF antigens.

The terms "a" and "an" herein do not denote a limitation of quantity, but rather denote the presence of at least one of the referenced item.

All ranges disclosed herein are inclusive and combinable. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated herein by reference in their entirety.

The invention claimed is:

1. A device for detection of the presence or absence of cerebrospinal fluid in a sample, comprising
   a sample application region,
   a sample labeling region comprising a first antibody to a CSF-enriched protein, wherein the first antibody is conjugated to a mobile particle;
   a sample detection region comprising a second antibody to the CSF-enriched protein, wherein the second antibody is fixed to the sample detection region,
   wherein the presence of a detectable band in the sample detection region indicates the presence of cerebrospinal fluid in the sample, wherein the CSF-enriched protein is selected from the group consisting of SEQ ID NO:2, SEQ ID NO: 5, SEQ ID NO: 7 and SEQ ID NO: 8.

2. The device of claim 1, wherein the device further comprises additional two to ten different antibodies that each specifically binds a different CSF-enriched protein.

3. The device of claim 2, wherein the device provides a single combined result, or the device provides an individual result for each antibody.

4. The device of claim 2, wherein each antibody is employed at a subthreshold level.

5. The device of claim 1, wherein the device further comprises additional four to ten different antibodies that each specifically binds a different CSF-enriched protein, and wherein a positive test does not require binding to all antibodies.

6. The device of claim 1, further comprising quantitating the level of CSF-enriched protein in the sample.

7. A method for detecting the presence or absence of CSF in a sample, comprising
   contacting the sample with the device of claim 1, and
   detecting binding partner-CSF-enriched protein complexes if present, wherein the presence of detectable complexes indicates the presence of CSF in the sample.

8. The method of claim 7, further comprising quantitating the amount of the CSF-enriched protein in the sample.

9. The method of claim 7, wherein detecting comprises an in situ immunoassay.

10. The method of claim 7, wherein the sample is tissue, blood, serum, plasma, urine, nasal and ear effluents, saliva, sweat, or tears.

11. The method of claim 7, wherein the sample is from an individual suspected of having a brain injury.

12. The method of claim 7, wherein the device further comprises additional two to ten different antibodies that each specifically binds a different CSF-enriched protein.

13. The method of claim 12, wherein each antibody is employed at a subthreshold level.

14. The method of claim 7, wherein the device further comprises additional four to ten different antibodies that each specifically binds a different CSF-enriched protein, and wherein a positive test does not require binding to all antibodies.

* * * * *

```
                        SEQUENCE LISTING

<160> NUMBER OF SEQ ID NOS: 29

<210> SEQ ID NO 1
<211> LENGTH: 1210
<212> TYPE: PRT
<213> ORGANISM: Homo sapiens

<400> SEQUENCE: 1

Arg Ala Met Glu Pro Leu Leu Leu Gly Arg Gly Leu Ile Val Tyr Leu
1               5                   10                  15

Met Phe Leu Leu Leu Lys Phe Ser Lys Ala Ile Glu Ile Pro Ser Ser
            20                  25                  30

Val Gln Gln Val Pro Thr Ile Ile Lys Gln Ser Lys Val Gln Val Ala
        35                  40                  45

Phe Pro Phe Asp Glu Tyr Phe Gln Ile Glu Cys Glu Ala Lys Gly Asn
    50                  55                  60

Pro Glu Pro Thr Phe Ser Trp Thr Lys Asp Gly Asn Pro Phe Tyr Phe
65                  70                  75                  80

Thr Asp His Arg Ile Ile Pro Ser Asn Asn Ser Gly Thr Phe Arg Ile
                85                  90                  95

Pro Asn Glu Gly His Ile Ser His Phe Gln Gly Lys Tyr Arg Cys Phe
            100                 105                 110

Ala Ser Asn Lys Leu Gly Ile Ala Met Ser Glu Glu Ile Glu Phe Ile
        115                 120                 125

Val Pro Ser Val Pro Lys Phe Pro Lys Glu Lys Ile Asp Pro Leu Glu
    130                 135                 140

Val Glu Glu Gly Asp Pro Ile Val Leu Pro Cys Asn Pro Pro Lys Gly
145                 150                 155                 160
```

```
Leu Pro Pro Leu His Ile Tyr Trp Met Asn Ile Glu Leu Glu His Ile
                165                 170                 175

Glu Gln Asp Glu Arg Val Tyr Met Ser Gln Lys Gly Asp Leu Tyr Phe
            180                 185                 190

Ala Asn Val Glu Glu Lys Asp Ser Arg Asn Asp Tyr Cys Cys Phe Ala
        195                 200                 205

Ala Phe Pro Arg Leu Arg Thr Ile Val Gln Lys Met Pro Met Lys Leu
    210                 215                 220

Thr Val Asn Ser Ser Asn Ser Ile Lys Gln Arg Lys Pro Lys Leu Leu
225                 230                 235                 240

Leu Pro Pro Thr Glu Ser Gly Ser Glu Ser Ser Ile Thr Ile Leu Lys
                245                 250                 255

Gly Glu Ile Leu Leu Leu Glu Cys Phe Ala Glu Gly Leu Pro Thr Pro
            260                 265                 270

Gln Val Asp Trp Asn Lys Ile Gly Gly Asp Leu Pro Lys Gly Arg Glu
        275                 280                 285

Ala Lys Glu Asn Tyr Gly Lys Thr Leu Lys Ile Glu Asn Val Ser Tyr
    290                 295                 300

Gln Asp Lys Gly Asn Tyr Arg Cys Thr Ala Ser Asn Phe Leu Gly Thr
305                 310                 315                 320

Ala Thr His Asp Phe His Val Ile Val Glu Glu Pro Pro Arg Trp Thr
                325                 330                 335

Lys Lys Pro Gln Ser Ala Val Tyr Ser Thr Gly Ser Asn Gly Ile Leu
            340                 345                 350

Leu Cys Glu Ala Glu Gly Glu Pro Gln Pro Thr Ile Lys Trp Arg Val
        355                 360                 365

Asn Gly Ser Pro Val Asp Asn His Pro Phe Ala Gly Asp Val Val Phe
    370                 375                 380

Pro Arg Glu Ile Ser Phe Thr Asn Leu Gln Pro Asn His Thr Ala Val
385                 390                 395                 400

Tyr Gln Cys Glu Ala Ser Asn Val His Gly Thr Ile Leu Ala Asn Ala
                405                 410                 415

Asn Ile Asp Val Val Asp Val Arg Pro Leu Ile Gln Thr Lys Asp Gly
            420                 425                 430

Glu Asn Tyr Ala Thr Val Val Gly Tyr Ser Ala Phe Leu His Cys Glu
        435                 440                 445

Phe Phe Ala Ser Pro Glu Ala Val Val Ser Trp Gln Lys Val Glu Glu
    450                 455                 460

Val Lys Pro Leu Glu Gly Arg Arg Tyr His Ile Tyr Glu Asn Gly Thr
465                 470                 475                 480

Leu Gln Ile Asn Arg Thr Thr Glu Glu Asp Ala Gly Ser Tyr Ser Cys
                485                 490                 495

Trp Val Glu Asn Ala Ile Gly Lys Thr Ala Val Thr Ala Asn Leu Asp
            500                 505                 510

Ile Arg Asn Ala Thr Lys Leu Arg Val Ser Pro Lys Asn Pro Arg Ile
        515                 520                 525

Pro Lys Leu His Met Leu Glu Leu His Cys Ser Lys Cys Asp Ser
    530                 535                 540

His Leu Lys His Ser Leu Lys Leu Ser Trp Ser Lys Asp Gly Glu Ala
545                 550                 555                 560

Phe Glu Ile Asn Gly Thr Glu Asp Gly Arg Ile Ile Asp Gly Ala
                565                 570                 575

Asn Leu Thr Ile Ser Asn Val Thr Leu Glu Asp Gln Gly Ile Tyr Cys
            580                 585                 590
```

-continued

```
Cys Ser Ala His Thr Ala Leu Asp Ser Ala Asp Ile Thr Gln Val
        595                 600                 605
Thr Val Leu Asp Val Pro Asp Pro Glu Asn Leu His Leu Ser Glu
        610                 615                 620
Arg Gln Asn Arg Ser Val Arg Leu Thr Trp Glu Ala Gly Ala Asp His
625                 630                 635                 640
Asn Ser Asn Ile Ser Glu Tyr Ile Val Glu Phe Glu Gly Asn Lys Glu
                645                 650                 655
Glu Pro Gly Arg Trp Glu Glu Leu Thr Arg Val Gln Gly Lys Lys Thr
                660                 665                 670
Thr Val Ile Leu Pro Leu Ala Pro Phe Val Arg Tyr Gln Phe Arg Val
        675                 680                 685
Ile Ala Val Asn Glu Val Gly Arg Ser Gln Pro Ser Gln Pro Ser Asp
        690                 695                 700
His His Glu Thr Pro Pro Ala Ala Pro Asp Arg Asn Pro Gln Asn Ile
705                 710                 715                 720
Arg Val Gln Ala Ser Gln Pro Lys Glu Met Ile Ile Lys Trp Glu Pro
                725                 730                 735
Leu Lys Ser Met Glu Gln Asn Gly Pro Gly Leu Glu Tyr Arg Val Thr
                740                 745                 750
Trp Lys Pro Gln Gly Ala Pro Val Glu Trp Glu Glu Thr Val Thr
        755                 760                 765
Asn His Thr Leu Arg Val Met Thr Pro Ala Val Tyr Ala Pro Tyr Asp
770                 775                 780
Val Lys Val Gln Ala Ile Asn Gln Leu Gly Ser Gly Pro Asp Pro Gln
785                 790                 795                 800
Ser Val Thr Leu Tyr Ser Gly Glu Asp Tyr Pro Asp Thr Ala Pro Val
                805                 810                 815
Ile His Gly Val Asp Val Ile Asn Ser Thr Leu Val Lys Val Thr Trp
        820                 825                 830
Ser Thr Val Pro Lys Asp Arg Val His Gly Arg Leu Lys Gly Tyr Gln
        835                 840                 845
Ile Asn Trp Trp Lys Thr Lys Ser Leu Leu Asp Gly Arg Thr His Pro
        850                 855                 860
Lys Glu Val Asn Ile Leu Arg Phe Ser Gly Gln Arg Asn Ser Gly Met
865                 870                 875                 880
Val Pro Ser Leu Asp Ala Phe Ser Glu Phe His Leu Thr Val Leu Ala
                885                 890                 895
Tyr Asn Ser Lys Gly Ala Gly Pro Glu Ser Glu Pro Tyr Ile Phe Gln
                900                 905                 910
Thr Pro Glu Gly Val Pro Glu Gln Pro Thr Phe Leu Lys Val Ile Lys
        915                 920                 925
Val Asp Lys Asp Thr Ala Thr Leu Ser Trp Gly Leu Pro Lys Lys Leu
930                 935                 940
Asn Gly Asn Leu Thr Gly Tyr Leu Leu Gln Tyr Gln Ile Ile Asn Asp
945                 950                 955                 960
Thr Tyr Glu Ile Gly Glu Leu Asn Asp Ile Asn Ile Thr Thr Pro Ser
                965                 970                 975
Lys Pro Ser Trp His Leu Ser Asn Leu Asn Ala Thr Thr Lys Tyr Lys
                980                 985                 990
Phe Tyr Leu Arg Ala Cys Thr Ser  Gln Gly Cys Gly Lys  Pro Ile Thr
        995                 1000                 1005
Glu Glu  Ser Ser Thr Leu Gly  Glu Gly Ser Lys Gly  Ile Gly Lys
```

```
                  1010                1015                1020

Ile Ser Gly Val Asn Leu Thr Gln Lys Thr His Pro Val Glu Val
    1025                1030                1035

Phe Glu Pro Gly Ala Glu His Ile Val Arg Leu Met Thr Lys Asn
    1040                1045                1050

Trp Gly Asp Asn Asp Ser Ile Phe Gln Asp Val Ile Glu Thr Arg
    1055                1060                1065

Gly Arg Glu Tyr Ala Gly Leu Tyr Asp Asp Ile Ser Thr Gln Gly
    1070                1075                1080

Trp Phe Ile Gly Leu Met Cys Ala Ile Ala Leu Leu Thr Leu Leu
    1085                1090                1095

Leu Leu Thr Val Cys Phe Val Lys Arg Asn Arg Gly Gly Lys Tyr
    1100                1105                1110

Ser Val Lys Glu Lys Glu Asp Leu His Pro Asp Pro Glu Ile Gln
    1115                1120                1125

Ser Val Lys Asp Glu Thr Phe Gly Glu Tyr Ser Asp Ser Asp Glu
    1130                1135                1140

Lys Pro Leu Lys Gly Ser Leu Arg Ser Leu Asn Arg Asp Met Gln
    1145                1150                1155

Pro Thr Glu Ser Ala Asp Ser Leu Val Glu Tyr Gly Glu Gly Asp
    1160                1165                1170

His Gly Leu Phe Ser Glu Asp Gly Ser Phe Ile Gly Ala Tyr Ala
    1175                1180                1185

Gly Ser Lys Glu Lys Gly Ser Val Glu Ser Asn Gly Ser Ser Thr
    1190                1195                1200

Ala Thr Phe Pro Leu Arg Ala
    1205                1210

<210> SEQ ID NO 2
<211> LENGTH: 224
<212> TYPE: PRT
<213> ORGANISM: Homo sapiens

<400> SEQUENCE: 2

Ile Val Gly Gly Tyr Thr Cys Glu Glu Asn Ser Leu Pro Tyr Gln Val
1               5                   10                  15

Ser Leu Asn Ser Gly Ser His Phe Cys Gly Gly Ser Leu Ile Ser Glu
            20                  25                  30

Gln Trp Val Val Ser Ala Ala His Cys Tyr Lys Thr Arg Ile Gln Val
        35                  40                  45

Arg Leu Gly Glu His Asn Ile Lys Val Leu Glu Gly Asn Glu Gln Phe
    50                  55                  60

Ile Asn Ala Ala Lys Ile Ile Arg His Pro Lys Tyr Asn Arg Asp Thr
65                  70                  75                  80

Leu Asp Asn Asp Ile Met Leu Ile Lys Leu Ser Ser Pro Ala Val Ile
                85                  90                  95

Asn Ala Arg Val Ser Thr Ile Ser Leu Pro Thr Ala Pro Pro Ala Ala
            100                 105                 110

Gly Thr Glu Cys Leu Ile Ser Gly Trp Gly Asn Thr Leu Ser Phe Gly
        115                 120                 125

Ala Asp Tyr Pro Asp Glu Leu Lys Cys Leu Asp Ala Pro Val Leu Thr
    130                 135                 140

Gln Ala Glu Cys Lys Ala Ser Tyr Pro Gly Lys Ile Thr Asn Ser Met
145                 150                 155                 160

Phe Cys Val Gly Phe Leu Glu Gly Gly Lys Asp Ser Cys Gln Arg Asp
```

```
                            165                 170                 175
Ala Gly Gly Pro Val Val Cys Asn Gly Gln Leu Gln Gly Val Val Ser
            180                 185                 190

Trp Gly His Gly Cys Ala Trp Lys Asn Arg Pro Gly Val Tyr Thr Lys
            195                 200                 205

Val Tyr Asn Tyr Val Asp Trp Ile Lys Asp Thr Ile Ala Ala Asn Ser
210                 215                 220

<210> SEQ ID NO 3
<211> LENGTH: 1040
<212> TYPE: PRT
<213> ORGANISM: homo sapiens

<400> SEQUENCE: 3

Met Gly Thr Ala Thr Arg Arg Lys Pro His Leu Leu Leu Val Ala Ala
1               5                   10                  15

Val Ala Leu Val Ser Ser Ser Ala Trp Ser Ser Ala Leu Gly Ser Gln
            20                  25                  30

Thr Thr Phe Gly Pro Val Phe Glu Asp Gln Pro Leu Ser Val Leu Phe
        35                  40                  45

Pro Glu Glu Ser Thr Glu Glu Gln Val Leu Leu Ala Cys Arg Ala Arg
    50                  55                  60

Ala Ser Pro Pro Ala Thr Tyr Arg Trp Lys Met Asn Gly Thr Glu Met
65                  70                  75                  80

Lys Leu Glu Pro Gly Ser Arg His Gln Leu Val Gly Gly Asn Leu Val
                85                  90                  95

Ile Met Asn Pro Thr Lys Ala Gln Asp Ala Gly Val Tyr Gln Cys Leu
            100                 105                 110

Ala Ser Asn Pro Val Gly Thr Val Val Ser Arg Glu Ala Ile Leu Arg
        115                 120                 125

Phe Gly Phe Leu Gln Glu Phe Ser Lys Glu Glu Arg Asp Pro Val Lys
    130                 135                 140

Ala His Glu Gly Trp Gly Val Met Leu Pro Cys Asn Pro Pro Ala His
145                 150                 155                 160

Tyr Pro Gly Leu Ser Tyr Arg Trp Leu Leu Asn Glu Phe Pro Asn Phe
                165                 170                 175

Ile Pro Thr Asp Gly Arg His Phe Val Ser Gln Thr Thr Gly Asn Leu
            180                 185                 190

Tyr Ile Ala Arg Thr Asn Ala Ser Asp Leu Gly Asn Tyr Ser Cys Leu
        195                 200                 205

Ala Thr Ser His Met Asp Phe Ser Thr Lys Ser Val Phe Ser Lys Phe
    210                 215                 220

Ala Gln Leu Asn Leu Ala Ala Glu Asp Thr Arg Leu Phe Ala Pro Ser
225                 230                 235                 240

Ile Lys Ala Arg Phe Pro Ala Glu Thr Tyr Ala Leu Val Gly Gln Gln
                245                 250                 255

Val Thr Leu Glu Cys Phe Ala Phe Gly Asn Pro Val Pro Arg Ile Lys
            260                 265                 270

Trp Arg Lys Val Asp Gly Ser Leu Ser Pro Gln Trp Thr Thr Ala Glu
        275                 280                 285

Pro Thr Leu Gln Ile Pro Ser Val Ser Phe Glu Asp Glu Gly Thr Tyr
    290                 295                 300

Glu Cys Glu Ala Glu Asn Ser Lys Gly Arg Asp Thr Val Gln Gly Arg
305                 310                 315                 320

Ile Ile Val Gln Ala Gln Pro Glu Trp Leu Lys Val Ile Ser Asp Thr
```

```
                325                 330                 335
Glu Ala Asp Ile Gly Ser Asn Leu Arg Trp Gly Cys Ala Ala Gly
                340                 345                 350
Lys Pro Arg Pro Thr Val Arg Trp Leu Arg Asn Gly Glu Pro Leu Ala
                355                 360                 365
Ser Gln Asn Arg Val Glu Val Leu Ala Gly Asp Leu Arg Phe Ser Lys
                370                 375                 380
Leu Ser Leu Glu Asp Ser Gly Met Tyr Gln Cys Val Ala Glu Asn Lys
385                 390                 395                 400
His Gly Thr Ile Tyr Ala Ser Ala Glu Leu Ala Val Gln Ala Leu Ala
                405                 410                 415
Pro Asp Phe Arg Leu Asn Pro Val Arg Arg Leu Ile Pro Ala Ala Arg
                420                 425                 430
Gly Gly Glu Ile Leu Ile Pro Cys Gln Pro Arg Ala Ala Pro Lys Ala
                435                 440                 445
Val Val Leu Trp Ser Lys Gly Thr Glu Ile Leu Val Asn Ser Ser Arg
                450                 455                 460
Val Thr Val Thr Pro Asp Gly Thr Leu Ile Ile Arg Asn Ile Ser Arg
465                 470                 475                 480
Ser Asp Glu Gly Lys Tyr Thr Cys Phe Ala Glu Asn Phe Met Gly Lys
                485                 490                 495
Ala Asn Ser Thr Gly Ile Leu Ser Val Arg Asp Ala Thr Lys Ile Thr
                500                 505                 510
Leu Ala Pro Ser Ser Ala Asp Ile Asn Leu Gly Asp Asn Leu Thr Leu
                515                 520                 525
Gln Cys His Ala Ser His Asp Pro Thr Met Asp Leu Thr Phe Thr Trp
                530                 535                 540
Thr Leu Asp Asp Phe Pro Ile Asp Phe Asp Lys Pro Gly Gly His Tyr
545                 550                 555                 560
Arg Arg Thr Asn Val Lys Glu Thr Ile Gly Asp Leu Thr Ile Leu Asn
                565                 570                 575
Ala Gln Leu Arg His Gly Gly Lys Tyr Thr Cys Met Ala Gln Thr Val
                580                 585                 590
Val Asp Ser Ala Ser Lys Glu Ala Thr Val Leu Val Arg Gly Pro Pro
                595                 600                 605
Gly Pro Pro Gly Gly Val Val Arg Asp Ile Gly Asp Thr Thr Ile
                610                 615                 620
Gln Leu Ser Trp Ser Arg Gly Phe Asp Asn His Ser Pro Ile Ala Lys
625                 630                 635                 640
Tyr Thr Leu Gln Ala Arg Thr Pro Pro Ala Gly Lys Trp Lys Gln Val
                645                 650                 655
Arg Thr Asn Pro Ala Asn Ile Glu Gly Asn Ala Glu Thr Ala Gln Val
                660                 665                 670
Leu Gly Leu Thr Pro Trp Met Asp Tyr Glu Phe Arg Val Ile Ala Ser
                675                 680                 685
Asn Ile Leu Gly Thr Gly Glu Pro Ser Gly Pro Ser Ser Lys Ile Arg
                690                 695                 700
Thr Arg Glu Ala Ala Pro Ser Val Ala Pro Ser Gly Leu Ser Gly Gly
705                 710                 715                 720
Gly Gly Ala Pro Gly Glu Leu Ile Val Asn Trp Thr Pro Met Ser Arg
                725                 730                 735
Glu Tyr Gln Asn Gly Asp Gly Phe Gly Tyr Leu Leu Ser Phe Arg Arg
                740                 745                 750
```

```
Gln Gly Ser Thr His Trp Gln Thr Ala Arg Val Pro Gly Ala Asp Ala
        755                 760                 765

Gln Tyr Phe Val Tyr Ser Asn Glu Ser Val Arg Pro Tyr Thr Pro Phe
    770                 775                 780

Glu Val Lys Ile Arg Ser Tyr Asn Arg Arg Gly Asp Gly Pro Glu Ser
785                 790                 795                 800

Leu Thr Ala Leu Val Tyr Ser Ala Glu Glu Pro Arg Val Ala Pro
                805                 810                 815

Thr Lys Val Trp Ala Lys Gly Val Ser Ser Ser Glu Met Asn Val Thr
                820                 825                 830

Trp Glu Pro Val Gln Gln Asp Met Asn Gly Ile Leu Leu Gly Tyr Glu
                835                 840                 845

Ile Arg Tyr Trp Lys Ala Gly Asp Lys Glu Ala Ala Ala Asp Arg Val
    850                 855                 860

Arg Thr Ala Gly Leu Asp Thr Ser Ala Arg Val Ser Gly Leu His Pro
865                 870                 875                 880

Asn Thr Lys Tyr His Val Thr Val Arg Ala Tyr Asn Arg Ala Gly Thr
                885                 890                 895

Gly Pro Ala Ser Pro Ser Ala Asn Ala Thr Thr Met Lys Pro Pro Pro
            900                 905                 910

Arg Arg Pro Pro Gly Asn Ile Ser Trp Thr Phe Ser Ser Ser Ser Leu
            915                 920                 925

Ser Ile Lys Trp Asp Pro Val Val Pro Phe Arg Asn Glu Ser Ala Val
    930                 935                 940

Thr Gly Tyr Lys Met Leu Tyr Gln Asn Asp Leu His Leu Thr Pro Thr
945                 950                 955                 960

Leu His Leu Thr Gly Lys Asn Trp Ile Glu Ile Pro Val Pro Glu Asp
                965                 970                 975

Ile Gly His Ala Leu Val Gln Ile Arg Thr Thr Gly Pro Gly Gly Asp
                980                 985                 990

Gly Ile Pro Ala Glu Val His Ile Val Arg Asn Gly Gly Thr Ser Met
            995                 1000                1005

Met Val Glu Asn Met Ala Val Arg Pro Ala Pro His Pro Gly Thr
    1010                1015                1020

Val Ile Ser His Ser Val Ala Met Leu Ile Leu Ile Gly Ser Leu
    1025                1030                1035

Glu Leu
    1040

<210> SEQ ID NO 4
<211> LENGTH: 1007
<212> TYPE: PRT
<213> ORGANISM: homo sapiens

<400> SEQUENCE: 4

Met Lys Met Trp Leu Leu Val Ser His Leu Val Ile Ile Ser Ile Thr
1               5                   10                  15

Thr Cys Leu Ala Val Ser Glu Glu Asp Lys Gly Phe Gly Pro Ile Phe
            20                  25                  30

Glu Glu Gln Pro Ile Asn Thr Ile Tyr Pro Glu Glu Ser Leu Glu Gly
        35                  40                  45

Lys Val Ser Leu Asn Cys Arg Ala Arg Ala Ser Pro Phe Pro Val Tyr
    50                  55                  60

Lys Trp Arg Met Asn Asn Gly Asp Val Asp Leu Thr Ser Asp Arg Tyr
65                  70                  75                  80
```

-continued

```
Ser Met Val Gly Gly Asn Leu Val Ile Asn Asn Pro Asp Lys Gln Lys
                85                  90                  95

Asp Ala Gly Ile Tyr Tyr Cys Leu Ala Ser Asn Asn Tyr Gly Met Val
            100                 105                 110

Arg Ser Thr Glu Ala Thr Leu Ser Phe Gly Tyr Leu Asp Pro Phe Pro
        115                 120                 125

Pro Glu Glu Arg Pro Glu Val Arg Val Lys Glu Gly Lys Gly Met Val
    130                 135                 140

Leu Leu Cys Asp Pro Pro Tyr His Phe Pro Asp Asp Leu Ser Tyr Arg
145                 150                 155                 160

Trp Leu Leu Asn Glu Phe Pro Val Phe Ile Thr Met Asp Lys Arg Arg
                165                 170                 175

Phe Val Ser Gln Thr Asn Gly Asn Leu Tyr Ile Ala Asn Val Glu Ala
            180                 185                 190

Ser Asp Lys Gly Asn Tyr Ser Cys Phe Val Ser Ser Pro Ser Ile Thr
        195                 200                 205

Lys Ser Val Phe Ser Lys Phe Ile Pro Leu Ile Pro Ile Pro Glu Arg
    210                 215                 220

Thr Thr Lys Pro Tyr Pro Ala Asp Ile Val Val Gln Phe Lys Asp Val
225                 230                 235                 240

Tyr Ala Leu Met Gly Gln Asn Val Thr Leu Glu Cys Phe Ala Leu Gly
                245                 250                 255

Asn Pro Val Pro Asp Ile Arg Trp Arg Lys Val Leu Glu Pro Met Pro
            260                 265                 270

Ser Thr Ala Glu Ile Ser Thr Ser Gly Ala Val Leu Lys Ile Phe Asn
        275                 280                 285

Ile Gln Leu Glu Asp Glu Gly Ile Tyr Glu Cys Glu Ala Glu Asn Ile
    290                 295                 300

Arg Gly Lys Asp Lys His Gln Ala Arg Ile Tyr Val Gln Ala Phe Pro
305                 310                 315                 320

Glu Trp Val Glu His Ile Asn Asp Thr Glu Val Asp Ile Gly Ser Asp
                325                 330                 335

Leu Tyr Trp Pro Cys Val Ala Thr Gly Lys Pro Ile Pro Thr Ile Arg
            340                 345                 350

Trp Leu Lys Asn Gly Tyr Ala Tyr His Lys Gly Glu Leu Arg Leu Tyr
        355                 360                 365

Asp Val Thr Phe Glu Asn Ala Gly Met Tyr Gln Cys Ile Ala Glu Asn
    370                 375                 380

Thr Tyr Gly Ala Ile Tyr Ala Asn Ala Glu Leu Lys Ile Leu Ala Leu
385                 390                 395                 400

Ala Pro Thr Phe Glu Met Asn Pro Met Lys Lys Ile Leu Ala Ala
                405                 410                 415

Lys Gly Gly Arg Val Ile Ile Glu Cys Lys Pro Lys Ala Ala Pro Lys
            420                 425                 430

Pro Lys Phe Ser Trp Ser Lys Gly Thr Glu Trp Leu Val Asn Ser Ser
        435                 440                 445

Arg Ile Leu Ile Trp Glu Asp Gly Ser Leu Glu Ile Asn Asn Ile Thr
    450                 455                 460

Arg Asn Asp Gly Gly Ile Tyr Thr Cys Phe Ala Glu Asn Asn Arg Gly
465                 470                 475                 480

Lys Ala Asn Ser Thr Gly Thr Leu Val Ile Thr Asp Pro Thr Arg Ile
                485                 490                 495

Ile Leu Ala Pro Ile Asn Ala Asp Ile Thr Val Gly Glu Asn Ala Thr
            500                 505                 510
```

```
Met Gln Cys Ala Ala Ser Phe Asp Pro Ala Leu Asp Leu Thr Phe Val
            515                 520                 525

Trp Ser Phe Asn Gly Tyr Val Ile Asp Phe Asn Lys Glu Asn Ile His
        530                 535                 540

Tyr Gln Arg Asn Phe Met Leu Asp Ser Asn Gly Glu Leu Leu Ile Arg
545                 550                 555                 560

Asn Ala Gln Leu Lys His Ala Gly Arg Tyr Thr Cys Thr Ala Gln Thr
                565                 570                 575

Ile Val Asp Asn Ser Ser Ala Ser Ala Asp Leu Val Val Arg Gly Pro
            580                 585                 590

Pro Gly Pro Pro Gly Gly Leu Arg Ile Glu Asp Ile Arg Ala Thr Ser
        595                 600                 605

Val Ala Leu Thr Trp Ser Arg Gly Ser Asp Asn His Ser Pro Ile Ser
    610                 615                 620

Lys Tyr Thr Ile Gln Thr Lys Thr Ile Leu Ser Asp Asp Trp Lys Asp
625                 630                 635                 640

Ala Lys Thr Asp Pro Pro Ile Ile Glu Gly Asn Met Glu Ala Ala Arg
                645                 650                 655

Ala Val Asp Leu Ile Pro Trp Met Glu Tyr Glu Phe Arg Val Val Ala
            660                 665                 670

Thr Asn Thr Leu Gly Arg Gly Glu Pro Ser Ile Pro Ser Asn Arg Ile
        675                 680                 685

Lys Thr Asp Gly Ala Ala Pro Asn Val Ala Pro Ser Asp Val Gly Gly
    690                 695                 700

Gly Gly Gly Arg Asn Arg Glu Leu Thr Ile Thr Trp Ala Pro Leu Ser
705                 710                 715                 720

Arg Glu Tyr His Tyr Gly Asn Asn Phe Gly Tyr Ile Val Ala Phe Lys
                725                 730                 735

Pro Phe Asp Gly Glu Glu Trp Lys Lys Val Thr Val Thr Asn Pro Asp
            740                 745                 750

Thr Gly Arg Tyr Val His Lys Asp Glu Thr Met Ser Pro Ser Thr Ala
        755                 760                 765

Phe Gln Val Lys Val Lys Ala Phe Asn Asn Lys Gly Asp Gly Pro Tyr
    770                 775                 780

Ser Leu Val Ala Val Ile Asn Ser Ala Gln Asp Ala Pro Ser Glu Ala
785                 790                 795                 800

Pro Thr Glu Val Gly Val Lys Val Leu Ser Ser Ser Glu Ile Ser Val
                805                 810                 815

His Trp Glu His Val Leu Glu Lys Ile Val Glu Ser Tyr Gln Ile Arg
            820                 825                 830

Tyr Trp Ala Ala His Asp Lys Glu Glu Ala Ala Asn Arg Val Gln Val
        835                 840                 845

Thr Ser Gln Glu Tyr Ser Ala Arg Leu Glu Asn Leu Leu Pro Asp Thr
    850                 855                 860

Gln Tyr Phe Ile Glu Val Gly Ala Cys Asn Ser Ala Gly Cys Gly Pro
865                 870                 875                 880

Pro Ser Asp Met Ile Glu Ala Phe Thr Lys Lys Ala Pro Pro Ser Gln
                885                 890                 895

Pro Pro Arg Ile Ile Ser Ser Val Arg Ser Gly Ser Arg Tyr Ile Ile
            900                 905                 910

Thr Trp Asp His Val Val Ala Leu Ser Asn Glu Ser Thr Val Thr Gly
        915                 920                 925

Tyr Lys Val Leu Tyr Arg Pro Asp Gly Gln His Asp Gly Lys Leu Tyr
```

-continued

```
                930                 935                 940
Ser Thr His Lys His Ser Ile Glu Val Pro Ile Pro Arg Asp Gly Glu
945                 950                 955                 960

Tyr Val Glu Val Arg Ala His Ser Asp Gly Gly Asp Gly Val Val
                965                 970                 975

Ser Gln Val Lys Ile Ser Gly Ala Pro Thr Leu Ser Pro Ser Leu Leu
                980                 985                 990

Gly Leu Leu Pro Ala Phe Gly Ile Leu Val Tyr Leu Glu Phe
                995                 1000                1005

<210> SEQ ID NO 5
<211> LENGTH: 490
<212> TYPE: PRT
<213> ORGANISM: homo sapiens

<400> SEQUENCE: 5

Met Lys Thr Gly Leu Phe Phe Leu Cys Leu Leu Gly Thr Ala Ala Ala
1               5                   10                  15

Ile Pro Thr Asn Ala Arg Leu Leu Ser Asp His Ser Lys Pro Thr Ala
                20                  25                  30

Glu Thr Val Ala Pro Asp Asn Thr Ala Ile Pro Ser Leu Arg Ala Glu
            35                  40                  45

Ala Glu Glu Asn Glu Lys Glu Thr Ala Val Ser Thr Glu Asp Asn Thr
50                  55                  60

Gln Ser Asp Asp Ile Leu Glu Glu Ser Asp Gln Pro Thr Gln Val Ser
65                  70                  75                  80

Lys Met Gln Glu Asp Glu Phe Asp Gln Gly Asn Gln Glu Gln Glu Asp
                85                  90                  95

Asn Ser Asn Ala Glu Met Glu Glu Glu Asn Ala Ser Asn Val Asn Lys
                100                 105                 110

His Ile Gln Glu Thr Glu Trp Gln Ser Gln Glu Gly Lys Thr Gly Leu
                115                 120                 125

Glu Ala Ile Ser Asn His Lys Glu Thr Glu Glu Lys Thr Val Ser Glu
130                 135                 140

Ala Leu Leu Met Glu Pro Thr Asp Asp Gly Asn Thr Thr Pro Arg Asn
145                 150                 155                 160

His Gly Val Asp Asp Asp Gly Asp Asp Gly Asp Asp Gly Gly Thr
                165                 170                 175

Asp Gly Pro Arg His Ser Ala Ser Asp Asp Tyr Phe Ile Pro Ser Gln
                180                 185                 190

Ala Phe Leu Glu Ala Glu Arg Ala Gln Ser Ile Ala Tyr His Leu Lys
            195                 200                 205

Ile Glu Glu Gln Arg Glu Lys Val His Glu Asn Glu Asn Ile Gly Thr
        210                 215                 220

Thr Glu Pro Gly Glu His Gln Glu Ala Lys Lys Ala Glu Asn Ser Ser
225                 230                 235                 240

Asn Glu Glu Glu Thr Ser Ser Glu Gly Asn Met Arg Val His Ala Val
                245                 250                 255

Asp Ser Cys Met Ser Phe Gln Cys Lys Arg Gly His Ile Cys Lys Ala
                260                 265                 270

Asp Gln Gln Gly Lys Pro His Cys Val Cys Gln Asp Pro Val Thr Cys
            275                 280                 285

Pro Pro Thr Lys Pro Leu Asp Gln Val Cys Gly Thr Asp Asn Gln Thr
        290                 295                 300

Tyr Ala Ser Ser Cys His Leu Phe Ala Thr Lys Cys Arg Leu Glu Gly
```

```
                    305                 310                 315                 320
Thr Lys Lys Gly His Gln Leu Gln Leu Asp Tyr Phe Gly Ala Cys Lys
                325                 330                 335

Ser Ile Pro Thr Cys Thr Asp Phe Glu Val Ile Gln Phe Pro Leu Arg
            340                 345                 350

Met Arg Asp Trp Leu Lys Asn Ile Leu Met Gln Leu Tyr Glu Ala Asn
        355                 360                 365

Ser Glu His Ala Gly Tyr Leu Asn Glu Lys Gln Arg Asn Lys Val Lys
    370                 375                 380

Lys Ile Tyr Leu Asp Glu Lys Arg Leu Leu Ala Gly Asp His Pro Ile
385                 390                 395                 400

Asp Leu Leu Arg Asp Phe Lys Lys Asn Tyr His Met Tyr Val Tyr
                405                 410                 415

Pro Val His Trp Gln Phe Ser Glu Leu Asp Gln His Pro Met Asp Arg
                420                 425                 430

Val Leu Thr His Ser Glu Leu Ala Pro Leu Arg Ala Ser Leu Val Pro
                435                 440                 445

Met Glu His Cys Ile Thr Arg Phe Phe Glu Glu Cys Asp Pro Asn Lys
            450                 455                 460

Asp Lys His Ile Thr Leu Lys Glu Trp Gly His Cys Phe Gly Ile Lys
465                 470                 475                 480

Glu Glu Asp Ile Asp Glu Asn Leu Leu Phe
                485                 490

<210> SEQ ID NO 6
<211> LENGTH: 771
<212> TYPE: PRT
<213> ORGANISM: homo sapiens

<400> SEQUENCE: 6

Met Gln Leu Lys Ile Met Pro Lys Lys Arg Leu Ser Ala Gly Arg
1               5                   10                  15

Val Pro Leu Ile Leu Phe Leu Cys Gln Met Ile Ser Ala Leu Glu Val
            20                  25                  30

Pro Leu Asp Leu Val Gln Pro Thr Ile Thr Gln Ser Pro Lys
        35                  40                  45

Asp Tyr Ile Ile Asp Pro Arg Glu Asn Ile Val Ile Gln Cys Glu Ala
    50                  55                  60

Lys Gly Lys Pro Pro Ser Phe Ser Trp Thr Arg Asn Gly Thr His
65                  70                  75                  80

Phe Asp Ile Asp Lys Asp Pro Leu Val Thr Met Lys Pro Gly Thr Gly
                85                  90                  95

Thr Leu Ile Ile Asn Ile Met Ser Glu Gly Lys Ala Glu Thr Tyr Glu
            100                 105                 110

Gly Val Tyr Gln Cys Thr Ala Arg Asn Glu Arg Gly Ala Ala Val Ser
        115                 120                 125

Asn Asn Ile Val Val Arg Pro Ser Arg Ser Pro Leu Trp Thr Lys Glu
    130                 135                 140

Lys Leu Glu Pro Ile Thr Leu Gln Ser Gly Gln Ser Leu Val Leu Pro
145                 150                 155                 160

Cys Arg Pro Pro Ile Gly Leu Pro Pro Ile Ile Phe Trp Met Asp
                165                 170                 175

Asn Ser Phe Gln Arg Leu Pro Gln Ser Glu Arg Val Ser Gln Gly Leu
            180                 185                 190

Asn Gly Asp Leu Tyr Phe Ser Asn Val Leu Pro Glu Asp Thr Arg Glu
```

-continued

```
                195                 200                 205
Asp Tyr Ile Cys Tyr Ala Arg Phe Asn His Thr Gln Thr Ile Gln Gln
210                 215                 220

Lys Gln Pro Ile Ser Val Lys Val Ile Ser Val Asp Glu Leu Asn Asp
225                 230                 235                 240

Thr Ile Ala Ala Asn Leu Ser Asp Thr Glu Phe Tyr Gly Ala Lys Ser
                245                 250                 255

Ser Arg Glu Arg Pro Pro Thr Phe Leu Thr Pro Glu Gly Asn Ala Ser
            260                 265                 270

Asn Lys Glu Glu Leu Arg Gly Asn Val Leu Ser Leu Glu Cys Ile Ala
        275                 280                 285

Glu Gly Leu Pro Thr Pro Ile Ile Tyr Trp Ala Lys Glu Asp Gly Met
290                 295                 300

Leu Pro Lys Asn Arg Thr Val Tyr Lys Asn Phe Glu Lys Thr Leu Gln
305                 310                 315                 320

Ile Ile His Val Ser Glu Ala Asp Ser Gly Asn Tyr Gln Cys Ile Ala
                325                 330                 335

Lys Asn Ala Leu Gly Ala Ile His His Thr Ile Ser Val Arg Val Lys
            340                 345                 350

Ala Ala Pro Tyr Trp Ile Thr Ala Pro Gln Asn Leu Val Leu Ser Pro
        355                 360                 365

Gly Glu Asp Gly Thr Leu Ile Cys Arg Ala Asn Gly Asn Pro Lys Pro
370                 375                 380

Arg Ile Ser Trp Leu Thr Asn Gly Val Pro Ile Glu Ile Ala Pro Asp
385                 390                 395                 400

Asp Pro Ser Arg Lys Ile Asp Gly Asp Thr Ile Ile Phe Ser Asn Val
                405                 410                 415

Gln Glu Arg Ser Ser Ala Val Tyr Gln Cys Asn Ala Ser Asn Glu Tyr
            420                 425                 430

Gly Tyr Leu Leu Ala Asn Ala Phe Val Asn Val Leu Ala Glu Pro Pro
        435                 440                 445

Arg Ile Leu Thr Pro Ala Asn Thr Leu Tyr Gln Val Ile Ala Asn Arg
450                 455                 460

Pro Ala Leu Leu Asp Cys Ala Phe Phe Gly Ser Pro Leu Pro Thr Ile
465                 470                 475                 480

Glu Trp Phe Lys Gly Ala Lys Gly Ser Ala Leu His Glu Asp Ile Tyr
                485                 490                 495

Val Leu His Glu Asn Gly Thr Leu Glu Ile Pro Val Ala Gln Lys Asp
            500                 505                 510

Ser Thr Gly Thr Tyr Thr Cys Val Ala Arg Asn Lys Leu Gly Met Ala
        515                 520                 525

Lys Asn Glu Val His Leu Glu Ile Lys Asp Ala Thr Trp Ile Val Lys
530                 535                 540

Gln Pro Glu Tyr Ala Val Val Gln Arg Gly Ser Met Val Ser Phe Glu
545                 550                 555                 560

Cys Lys Val Lys His Asp His Thr Leu Ser Leu Thr Val Leu Trp Leu
                565                 570                 575

Lys Asp Asn Arg Glu Leu Pro Ser Asp Glu Arg Phe Thr Val Asp Lys
            580                 585                 590

Asp His Leu Val Val Ala Asp Val Ser Asp Asp Ser Gly Thr Tyr
        595                 600                 605

Thr Cys Val Ala Asn Thr Thr Leu Asp Ser Val Ser Ala Ser Ala Val
610                 615                 620
```

-continued

Leu Ser Val Val Asp Val Pro Asn Pro Phe Asp Leu Glu Leu Thr
625                 630                 635                 640

Asp Gln Leu Asp Lys Ser Val Gln Leu Ser Trp Thr Pro Gly Asp Asp
            645                 650                 655

Asn Asn Ser Pro Ile Thr Lys Phe Ile Ile Glu Tyr Glu Asp Ala Met
                660                 665                 670

His Lys Pro Gly Leu Trp His His Gln Thr Glu Val Ser Gly Thr Gln
            675                 680                 685

Thr Thr Ala Gln Leu Lys Leu Ser Pro Tyr Val Asn Tyr Ser Phe Arg
        690                 695                 700

Val Met Ala Val Asn Ser Ile Gly Lys Ser Leu Pro Ser Glu Ala Ser
705                 710                 715                 720

Glu Gln Tyr Leu Thr Lys Ala Ser Glu Pro Asp Lys Asn Pro Thr Ala
                725                 730                 735

Val Glu Gly Leu Gly Ser Glu Pro Asp Asn Leu Val Ile Thr Trp Lys
            740                 745                 750

Pro Leu Asn Gly Phe Glu Ser Asn Gly Pro Gly Leu Gln Thr Ser Thr
        755                 760                 765

Ala Ser Phe
    770

<210> SEQ ID NO 7
<211> LENGTH: 1180
<212> TYPE: PRT
<213> ORGANISM: homo sapiens

<400> SEQUENCE: 7

Met Gln Leu Lys Ile Met Pro Lys Lys Arg Leu Ser Ala Gly Arg
1               5                   10                  15

Val Pro Leu Ile Leu Phe Leu Cys Gln Met Ile Ser Ala Leu Glu Val
            20                  25                  30

Pro Leu Asp Pro Lys Leu Leu Glu Asp Leu Val Gln Pro Pro Thr Ile
        35                  40                  45

Thr Gln Gln Ser Pro Lys Asp Tyr Ile Ile Asp Pro Arg Glu Asn Ile
    50                  55                  60

Val Ile Gln Cys Glu Ala Lys Gly Lys Pro Pro Pro Ser Phe Ser Trp
65                  70                  75                  80

Thr Arg Asn Gly Thr His Phe Asp Ile Asp Lys Asp Pro Leu Val Thr
                85                  90                  95

Met Lys Pro Gly Thr Gly Thr Leu Ile Ile Asn Ile Met Ser Glu Gly
            100                 105                 110

Lys Ala Glu Thr Tyr Glu Gly Val Tyr Gln Cys Thr Ala Arg Asn Glu
        115                 120                 125

Arg Gly Ala Ala Val Ser Asn Asn Ile Val Val Arg Pro Ser Arg Ser
    130                 135                 140

Pro Leu Trp Thr Lys Glu Lys Leu Glu Pro Ile Thr Leu Gln Ser Gly
145                 150                 155                 160

Gln Ser Leu Val Leu Pro Cys Arg Pro Pro Ile Gly Leu Pro Pro Pro
                165                 170                 175

Ile Ile Phe Trp Met Asp Asn Ser Phe Gln Arg Leu Pro Gln Ser Glu
            180                 185                 190

Arg Val Ser Gln Gly Leu Asn Gly Asp Leu Tyr Phe Ser Asn Val Leu
        195                 200                 205

Pro Glu Asp Thr Arg Glu Asp Tyr Ile Cys Tyr Ala Arg Phe Asn His
    210                 215                 220

```
Thr Gln Thr Ile Gln Gln Lys Gln Pro Ile Ser Val Lys Val Ile Ser
225                 230                 235                 240

Ala Lys Ser Ser Arg Glu Arg Pro Pro Thr Phe Leu Thr Pro Glu Gly
            245                 250                 255

Asn Ala Ser Asn Lys Glu Glu Leu Arg Gly Asn Val Leu Ser Leu Glu
        260                 265                 270

Cys Ile Ala Glu Gly Leu Pro Thr Pro Ile Ile Tyr Trp Ala Lys Glu
    275                 280                 285

Asp Gly Met Leu Pro Lys Asn Arg Thr Val Tyr Lys Asn Phe Glu Lys
        290                 295                 300

Thr Leu Gln Ile Ile His Val Ser Glu Ala Asp Ser Gly Asn Tyr Gln
305                 310                 315                 320

Cys Ile Ala Lys Asn Ala Leu Gly Ala Ile His His Thr Ile Ser Val
            325                 330                 335

Arg Val Lys Ala Ala Pro Tyr Trp Ile Thr Ala Pro Gln Asn Leu Val
        340                 345                 350

Leu Ser Pro Gly Glu Asp Gly Thr Leu Ile Cys Arg Ala Asn Gly Asn
            355                 360                 365

Pro Lys Pro Arg Ile Ser Trp Leu Thr Asn Gly Val Pro Ile Glu Ile
    370                 375                 380

Ala Pro Asp Asp Pro Ser Arg Lys Ile Asp Gly Asp Thr Ile Ile Phe
385                 390                 395                 400

Ser Asn Val Gln Glu Arg Ser Ser Ala Val Tyr Gln Cys Asn Ala Ser
                405                 410                 415

Asn Glu Tyr Gly Tyr Leu Leu Ala Asn Ala Phe Val Asn Val Leu Ala
            420                 425                 430

Glu Pro Pro Arg Ile Leu Thr Pro Ala Asn Thr Leu Tyr Gln Val Ile
        435                 440                 445

Ala Asn Arg Pro Ala Leu Leu Asp Cys Ala Phe Phe Gly Ser Pro Leu
450                 455                 460

Pro Thr Ile Glu Trp Phe Lys Gly Ala Lys Gly Ser Ala Leu His Glu
465                 470                 475                 480

Asp Ile Tyr Val Leu His Glu Asn Gly Thr Leu Glu Ile Pro Val Ala
                485                 490                 495

Gln Lys Asp Ser Thr Gly Thr Tyr Thr Cys Val Ala Arg Asn Lys Leu
                500                 505                 510

Gly Met Ala Lys Asn Glu Val His Leu Glu Ile Lys Asp Ala Thr Trp
            515                 520                 525

Ile Val Lys Gln Pro Glu Tyr Ala Val Val Gln Arg Gly Ser Met Val
        530                 535                 540

Ser Phe Glu Cys Lys Val Lys His Asp His Thr Leu Ser Leu Thr Val
545                 550                 555                 560

Leu Trp Leu Lys Asp Asn Arg Glu Leu Pro Ser Asp Glu Arg Phe Thr
                565                 570                 575

Val Asp Lys Asp His Leu Val Val Ala Asp Val Ser Asp Asp Asp Ser
                580                 585                 590

Gly Thr Tyr Thr Cys Val Ala Asn Thr Leu Asp Ser Val Ser Ala
            595                 600                 605

Ser Ala Val Leu Ser Val Ala Pro Thr Pro Ala Pro Val
610                 615                 620

Tyr Asp Val Pro Asn Pro Phe Asp Leu Glu Leu Thr Asp Gln Leu
625                 630                 635                 640

Asp Lys Ser Val Gln Leu Ser Trp Thr Pro Gly Asp Asp Asn Asn Ser
                645                 650                 655
```

```
Pro Ile Thr Lys Phe Ile Ile Glu Tyr Glu Asp Ala Met His Lys Pro
        660                 665                 670

Gly Leu Trp His His Gln Thr Glu Val Ser Gly Thr Gln Thr Thr Ala
        675                 680                 685

Gln Leu Lys Leu Ser Pro Tyr Val Asn Tyr Ser Phe Arg Val Met Ala
        690                 695                 700

Val Asn Ser Ile Gly Lys Ser Leu Pro Ser Glu Ala Ser Glu Gln Tyr
705                 710                 715                 720

Leu Thr Lys Ala Ser Glu Pro Asp Lys Asn Pro Thr Ala Val Glu Gly
            725                 730                 735

Leu Gly Ser Glu Pro Asp Asn Leu Val Ile Thr Trp Lys Pro Leu Asn
            740                 745                 750

Gly Phe Glu Ser Asn Gly Pro Gly Leu Gln Tyr Lys Val Ser Trp Arg
        755                 760                 765

Gln Lys Asp Gly Asp Asp Glu Trp Thr Ser Val Val Val Ala Asn Val
        770                 775                 780

Ser Lys Tyr Ile Val Ser Gly Thr Pro Thr Phe Val Pro Tyr Leu Ile
785                 790                 795                 800

Lys Val Gln Ala Leu Asn Asp Met Gly Phe Ala Pro Glu Pro Ala Val
                805                 810                 815

Val Met Gly His Ser Gly Glu Asp Leu Pro Met Val Ala Pro Gly Asn
            820                 825                 830

Val Arg Val Asn Val Val Asn Ser Thr Leu Ala Glu Val His Trp Asp
        835                 840                 845

Pro Val Pro Leu Lys Ser Ile Arg Gly His Leu Gln Gly Tyr Arg Ile
850                 855                 860

Tyr Tyr Trp Lys Thr Gln Ser Ser Ser Lys Arg Asn Arg Arg His Ile
865                 870                 875                 880

Glu Lys Lys Ile Leu Thr Phe Gln Gly Ser Lys Thr His Gly Met Leu
                885                 890                 895

Pro Gly Leu Glu Pro Phe Ser His Tyr Thr Leu Asn Val Arg Val Val
            900                 905                 910

Asn Gly Lys Gly Glu Gly Pro Ala Ser Pro Asp Arg Val Phe Asn Thr
        915                 920                 925

Pro Glu Gly Val Pro Ser Ala Pro Ser Ser Leu Lys Ile Val Asn Pro
930                 935                 940

Thr Leu Asp Ser Leu Thr Leu Glu Trp Asp Pro Pro Ser His Pro Asn
945                 950                 955                 960

Gly Ile Leu Thr Glu Tyr Thr Leu Lys Tyr Gln Pro Ile Asn Ser Thr
                965                 970                 975

His Glu Leu Gly Pro Leu Val Asp Leu Lys Ile Pro Ala Asn Lys Thr
            980                 985                 990

Arg Trp Thr Leu Lys Asn Leu Asn Phe Ser Thr Arg Tyr Lys Phe Tyr
        995                 1000                1005

Phe Tyr Ala Gln Thr Ser Ala Gly Ser Gly Ser Gln Ile Thr Glu
    1010                1015                1020

Glu Ala Val Thr Thr Val Asp Glu Ala Met Ala Ser Arg Gln Val
    1025                1030                1035

Asp Ile Ala Thr Gln Gly Trp Phe Ile Gly Leu Met Cys Ala Val
    1040                1045                1050

Ala Leu Leu Ile Leu Ile Leu Leu Ile Val Cys Phe Ile Arg Arg
    1055                1060                1065

Asn Lys Gly Gly Lys Tyr Pro Val Lys Glu Lys Glu Asp Ala His
```

```
                      1070              1075                1080
Ala Asp Pro Glu Ile Gln Pro Met Lys Glu Asp Asp Gly Thr Phe
    1085                1090                1095

Gly Glu Tyr Ser Asp Ala Glu Asp His Lys Pro Leu Lys Lys Gly
    1100                1105                1110

Ser Arg Thr Pro Ser Asp Arg Thr Val Lys Lys Glu Asp Ser Asp
    1115                1120                1125

Asp Ser Leu Val Asp Tyr Gly Glu Gly Val Asn Gly Gln Phe Asn
    1130                1135                1140

Glu Asp Gly Ser Phe Ile Gly Gln Tyr Ser Gly Lys Lys Glu Lys
    1145                1150                1155

Glu Pro Ala Glu Gly Asn Glu Ser Ser Glu Ala Pro Ser Pro Val
    1160                1165                1170

Asn Ala Met Asn Ser Phe Val
    1175                1180

<210> SEQ ID NO 8
<211> LENGTH: 818
<212> TYPE: PRT
<213> ORGANISM: homo sapiens

<400> SEQUENCE: 8

Leu Leu Gln Val Thr Ile Ser Leu Ser Lys Val Glu Leu Ser Val Gly
1               5                   10                  15

Glu Ser Lys Phe Phe Thr Cys Thr Ala Ile Gly Glu Pro Glu Ser Ile
            20                  25                  30

Asp Trp Tyr Asn Pro Gln Gly Glu Lys Ile Ile Ser Thr Gln Arg Val
        35                  40                  45

Val Val Gln Lys Glu Gly Val Arg Ser Arg Leu Thr Ile Tyr Asn Ala
    50                  55                  60

Asn Ile Glu Asp Ala Gly Ile Tyr Arg Cys Gln Ala Thr Asp Ala Lys
65                  70                  75                  80

Gly Gln Thr Gln Glu Ala Thr Val Val Leu Glu Ile Tyr Gln Lys Leu
                85                  90                  95

Thr Phe Arg Glu Val Val Ser Pro Gln Glu Phe Lys Gln Gly Glu Asp
            100                 105                 110

Ala Glu Val Val Cys Arg Val Ser Ser Pro Ala Pro Ala Val Ser
        115                 120                 125

Trp Leu Tyr His Asn Glu Glu Val Thr Thr Ile Ser Asp Asn Arg Phe
    130                 135                 140

Ala Met Leu Ala Asn Asn Asn Leu Gln Ile Leu Asn Ile Asn Lys Ser
145                 150                 155                 160

Asp Glu Gly Ile Tyr Arg Cys Glu Gly Arg Val Glu Ala Arg Gly Glu
                165                 170                 175

Ile Asp Phe Arg Asp Ile Ile Val Ile Val Asn Val Pro Pro Ala Ile
            180                 185                 190

Ser Met Pro Gln Lys Ser Phe Asn Ala Thr Ala Glu Arg Gly Glu Glu
        195                 200                 205

Met Thr Phe Ser Cys Arg Ala Ser Gly Ser Pro Glu Pro Ala Ile Ser
    210                 215                 220

Trp Phe Arg Asn Gly Lys Leu Ile Glu Glu Asn Glu Lys Tyr Ile Leu
225                 230                 235                 240

Lys Gly Ser Asn Thr Glu Leu Thr Val Arg Asn Ile Ile Asn Ser Asp
                245                 250                 255

Gly Gly Pro Tyr Val Cys Arg Ala Thr Asn Lys Ala Gly Glu Asp Glu
```

-continued

```
                    260                 265                 270
Lys Gln Ala Phe Leu Gln Val Phe Val Gln Pro His Ile Ile Gln Leu
            275                 280                 285

Lys Asn Glu Thr Thr Tyr Glu Asn Gly Gln Val Thr Leu Val Cys Asp
        290                 295                 300

Ala Glu Gly Glu Pro Ile Pro Glu Ile Thr Trp Lys Arg Ala Val Asp
305                 310                 315                 320

Gly Phe Thr Phe Thr Glu Gly Asp Lys Ser Leu Asp Gly Arg Ile Glu
                325                 330                 335

Val Lys Gly Gln His Gly Ser Ser Leu His Ile Lys Asp Val Lys
            340                 345                 350

Leu Ser Asp Ser Gly Arg Tyr Asp Cys Glu Ala Ser Arg Ile Gly
        355                 360                 365

Gly His Gln Lys Ser Met Tyr Leu Asp Ile Glu Tyr Ala Pro Lys Phe
    370                 375                 380

Ile Ser Asn Gln Thr Ile Tyr Tyr Ser Trp Glu Gly Asn Pro Ile Asn
385                 390                 395                 400

Ile Ser Cys Asp Val Lys Ser Asn Pro Pro Ala Ser Ile His Trp Arg
                405                 410                 415

Arg Asp Lys Leu Val Leu Pro Ala Lys Asn Thr Thr Asn Leu Lys Thr
            420                 425                 430

Tyr Ser Thr Gly Arg Lys Met Ile Leu Glu Ile Ala Pro Thr Ser Asp
        435                 440                 445

Asn Asp Phe Gly Arg Tyr Asn Cys Thr Ala Thr Asn His Ile Gly Thr
    450                 455                 460

Arg Phe Gln Glu Tyr Ile Leu Ala Leu Ala Asp Val Pro Ser Ser Pro
465                 470                 475                 480

Tyr Gly Val Lys Ile Ile Glu Leu Ser Gln Thr Thr Ala Lys Val Ser
                485                 490                 495

Phe Asn Lys Pro Asp Ser His Gly Gly Val Pro Ile His His Tyr Gln
            500                 505                 510

Val Asp Val Lys Glu Val Ala Ser Glu Ile Trp Lys Ile Val Arg Ser
        515                 520                 525

His Gly Val Gln Thr Met Val Val Leu Asn Asn Leu Glu Pro Asn Thr
    530                 535                 540

Thr Tyr Glu Ile Arg Val Ala Ala Val Asn Gly Lys Gly Gln Gly Asp
545                 550                 555                 560

Tyr Ser Lys Ile Glu Ile Phe Gln Thr Leu Pro Val Arg Glu Pro Ser
                565                 570                 575

Pro Pro Ser Ile His Gly Gln Pro Ser Ser Gly Lys Ser Phe Lys Leu
            580                 585                 590

Ser Ile Thr Lys Gln Asp Asp Gly Gly Ala Pro Ile Leu Glu Tyr Ile
        595                 600                 605

Val Lys Tyr Arg Ser Lys Asp Lys Glu Asp Gln Trp Leu Glu Lys Lys
    610                 615                 620

Val Gln Gly Asn Lys Asp His Ile Ile Leu Glu His Leu Gln Trp Thr
625                 630                 635                 640

Met Gly Tyr Glu Val Gln Ile Thr Ala Ala Asn Arg Leu Gly Tyr Ser
                645                 650                 655

Glu Pro Thr Val Tyr Glu Phe Ser Met Pro Pro Lys Pro Asn Ile Ile
            660                 665                 670

Lys Asp Thr Leu Phe Asn Gly Leu Gly Leu Gly Ala Val Ile Gly Leu
        675                 680                 685
```

```
Gly Val Ala Ala Leu Leu Ile Leu Val Val Thr Asp Val Ser Cys
            690                 695                 700
Phe Phe Ile Arg Gln Cys Gly Leu Leu Met Cys Ile Thr Arg Arg Met
705                 710                 715                 720
Cys Gly Lys Lys Ser Gly Ser Ser Gly Lys Ser Lys Glu Leu Glu Glu
                725                 730                 735
Gly Lys Ala Ala Tyr Leu Lys Asp Gly Ser Lys Glu Pro Ile Val Glu
                740                 745                 750
Met Arg Thr Glu Asp Glu Arg Val Thr Asn His Glu Asp Gly Ser Pro
            755                 760                 765
Val Asn Glu Pro Asn Glu Thr Thr Pro Leu Thr Glu Pro Glu Lys Leu
            770                 775                 780
Pro Leu Lys Glu Glu Asp Gly Lys Glu Ala Leu Asn Pro Glu Thr Ile
785                 790                 795                 800
Glu Ile Lys Val Ser Asn Asp Ile Ile Gln Ser Lys Glu Asp Asp Ser
                805                 810                 815
Lys Ala

<210> SEQ ID NO 9
<211> LENGTH: 287
<212> TYPE: PRT
<213> ORGANISM: homo sapiens

<400> SEQUENCE: 9

Met Gly Asn Ala Met Phe Val Lys Glu Gln Leu Ser Leu Leu Asp Arg
1               5                   10                  15
Phe Thr Glu Asp Ala Lys Arg Leu Tyr Gly Ser Glu Ala Phe Ala Thr
            20                  25                  30
Asp Phe Gln Asp Ser Ala Ala Lys Lys Leu Ile Asn Asp Tyr Val
            35                  40                  45
Lys Asn Gly Thr Arg Gly Lys Ile Thr Asp Leu Ile Lys Asn Leu Asp
    50                  55                  60
Ser Gln Thr Met Met Val Leu Val Asn Tyr Ile Phe Phe Lys Ala Lys
65                  70                  75                  80
Trp Glu Met Pro Phe Asp Pro Gln Asp Thr His Gln Ser Arg Phe Tyr
                85                  90                  95
Leu Asn Lys Lys Lys Trp Val Met Val Pro Met Met Ser Leu His His
                100                 105                 110
Leu Thr Ile Pro Tyr Phe Arg Asp Glu Glu Leu Ser Cys Thr Val Val
            115                 120                 125
Glu Leu Lys Tyr Thr Gly Asn Ala Ser Ala Leu Phe Ile Leu Pro Asp
    130                 135                 140
Gln Asp Lys Met Glu Glu Val Glu Ala Met Leu Leu Pro Glu Thr Leu
145                 150                 155                 160
Lys Arg Trp Arg Asp Ser Leu Glu Phe Arg Glu Ile Gly Glu Leu Tyr
                165                 170                 175
Leu Pro Lys Phe Ser Ile Ser Arg Asp Tyr Asn Leu Asn Asp Ile Leu
                180                 185                 190
Leu Gln Leu Gly Ile Glu Glu Ala Phe Thr Ser Lys Ala Asp Leu Ser
            195                 200                 205
Gly Ile Thr Gly Ala Arg Asn Leu Ala Val Ser Gln Val Val His Lys
    210                 215                 220
Ala Val Leu Asp Val Phe Glu Glu Gly Thr Glu Ala Ser Ala Ala Thr
225                 230                 235                 240
Ala Val Lys Ile Thr Leu Leu Ser Ala Leu Val Glu Thr Arg Thr Ile
```

```
                      245                 250                 255
Val Arg Phe Asn Arg Pro Phe Leu Met Ile Ile Val Pro Thr Asp Thr
            260                 265                 270
Gln Asn Ile Phe Phe Met Ser Lys Val Thr Asn Pro Lys Gln Ala
        275                 280                 285

<210> SEQ ID NO 10
<211> LENGTH: 338
<212> TYPE: PRT
<213> ORGANISM: homo sapiens

<400> SEQUENCE: 10

Met Arg Lys Arg Ala Pro Gln Ser Glu Met Ala Pro Ala Gly Val Ser
 1               5                  10                  15

Leu Arg Ala Thr Ile Leu Cys Leu Leu Ala Trp Ala Gly Leu Ala Ala
            20                  25                  30

Gly Asp Arg Val Tyr Ile His Pro Phe His Leu Val Ile His Asn Glu
        35                  40                  45

Ser Thr Cys Glu Gln Leu Ala Lys Ala Asn Ala Gly Lys Pro Lys Asp
    50                  55                  60

Pro Thr Phe Ile Pro Ala Pro Ile Gln Ala Lys Thr Ser Pro Val Asp
65                  70                  75                  80

Glu Lys Ala Leu Gln Asp Gln Leu Val Leu Val Ala Ala Lys Leu Asp
                85                  90                  95

Thr Glu Asp Lys Leu Arg Ala Ala Met Val Gly Met Leu Ala Asn Phe
            100                 105                 110

Leu Gly Phe Arg Ile Tyr Gly Met His Ser Glu Leu Trp Gly Val Val
        115                 120                 125

His Gly Ala Thr Val Leu Ser Pro Thr Ala Val Phe Gly Thr Leu Ala
    130                 135                 140

Ser Leu Tyr Leu Gly Ala Leu Asp His Thr Ala Asp Arg Leu Gln Ala
145                 150                 155                 160

Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
            180                 185                 190

Ala Gln Gly Arg Ala Asp Ser Gln Ala Gln Leu Leu Leu Ser Thr Val
        195                 200                 205

Val Gly Val Phe Thr Ala Pro Gly Leu His Leu Lys Gln Pro Phe Val
    210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Met Gly Ala Ser Val
            260                 265                 270

Asp Ser Thr Leu Ala Phe Asn Thr Tyr Val His Phe Gln Gly Lys Met
        275                 280                 285

Lys Gly Phe Ser Leu Leu Ala Glu Pro Gln Glu Phe Trp Val Asp Asn
    290                 295                 300

Ser Thr Ser Val Ser Val Pro Met Leu Ser Gly Met Gly Thr Phe Gln
305                 310                 315                 320

His Trp Ser Asp Ile Gln Asp Asn Phe Ser Val Thr Gln Val Pro Phe
                325                 330                 335

Thr Glu
```

<210> SEQ ID NO 11
<211> LENGTH: 485
<212> TYPE: PRT
<213> ORGANISM: homo sapiens

<400> SEQUENCE: 11

Met Arg Lys Arg Ala Pro Gln Ser Glu Met Ala Pro Ala Gly Val Ser
1               5                   10                  15

Leu Arg Ala Thr Ile Leu Cys Leu Leu Ala Trp Ala Gly Leu Ala Ala
            20                  25                  30

Gly Asp Arg Val Tyr Ile His Pro Phe His Leu Val Ile His Asn Glu
        35                  40                  45

Ser Thr Cys Glu Gln Leu Ala Lys Ala Asn Ala Gly Lys Pro Lys Asp
    50                  55                  60

Pro Thr Phe Ile Pro Ala Pro Ile Gln Ala Lys Thr Ser Pro Val Asp
65                  70                  75                  80

Glu Lys Ala Leu Gln Asp Gln Leu Val Leu Val Ala Ala Lys Leu Asp
                85                  90                  95

Thr Glu Asp Lys Leu Arg Ala Ala Met Val Gly Met Leu Ala Asn Phe
            100                 105                 110

Leu Gly Phe Arg Ile Tyr Gly Met His Ser Glu Leu Trp Gly Val Val
        115                 120                 125

His Gly Ala Thr Val Leu Ser Pro Thr Ala Val Phe Gly Thr Leu Ala
    130                 135                 140

Ser Leu Tyr Leu Gly Ala Leu Asp His Thr Ala Asp Arg Leu Gln Ala
145                 150                 155                 160

Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
            180                 185                 190

Ala Gln Gly Arg Ala Asp Ser Gln Ala Gln Leu Leu Leu Ser Thr Val
        195                 200                 205

Val Gly Val Phe Thr Ala Pro Gly Leu His Leu Lys Gln Pro Phe Val
    210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Met Gly Ala Ser Val
            260                 265                 270

Asp Ser Thr Leu Ala Phe Asn Thr Tyr Val His Phe Gln Gly Lys Met
        275                 280                 285

Lys Gly Phe Ser Leu Leu Ala Glu Pro Gln Glu Phe Trp Val Asp Asn
    290                 295                 300

Ser Thr Ser Val Ser Val Pro Met Leu Ser Gly Met Gly Thr Phe Gln
305                 310                 315                 320

His Trp Ser Asp Ile Gln Asp Asn Phe Ser Val Thr Gln Val Pro Phe
                325                 330                 335

Thr Glu Ser Ala Cys Leu Leu Leu Ile Gln Pro His Tyr Ala Ser Asp
            340                 345                 350

Leu Asp Lys Val Glu Gly Leu Thr Phe Gln Gln Asn Ser Leu Asn Trp
        355                 360                 365

Met Lys Lys Leu Ser Pro Arg Thr Ile His Leu Thr Met Pro Gln Leu
    370                 375                 380

```
Val Leu Gln Gly Ser Tyr Asp Leu Gln Asp Leu Leu Ala Gln Ala Glu
385                 390                 395                 400

Leu Pro Ala Ile Leu His Thr Glu Leu Asn Leu Gln Lys Leu Ser Asn
            405                 410                 415

Asp Arg Ile Arg Val Gly Glu Val Leu Asn Ser Ile Phe Phe Glu Leu
            420                 425                 430

Glu Ala Asp Glu Arg Glu Pro Thr Glu Ser Thr Gln Gln Leu Asn Lys
        435                 440                 445

Pro Glu Val Leu Glu Val Thr Leu Asn Arg Pro Phe Leu Phe Ala Val
        450                 455                 460

Tyr Asp Gln Ser Ala Thr Ala Leu His Phe Leu Gly Arg Val Ala Asn
465                 470                 475                 480

Pro Leu Ser Thr Ala
                485

<210> SEQ ID NO 12
<211> LENGTH: 398
<212> TYPE: PRT
<213> ORGANISM: homo sapiens

<400> SEQUENCE: 12

Met Gly Ala Pro Ala Ser Leu Leu Leu Leu Leu Leu Phe Ala
1               5                   10                  15

Cys Cys Trp Ala Pro Gly Gly Ala Asn Leu Ser Gln Asp Asp Ser Gln
                20                  25                  30

Pro Trp Thr Ser Asp Glu Thr Val Val Ala Gly Gly Thr Val Val Leu
            35                  40                  45

Lys Cys Gln Val Lys Asp His Glu Asp Ser Ser Leu Gln Trp Ser Asn
50                  55                  60

Pro Ala Gln Gln Thr Leu Tyr Phe Gly Glu Lys Arg Ala Leu Arg Asp
65                  70                  75                  80

Asn Arg Ile Gln Leu Val Thr Ser Thr Pro His Glu Leu Ser Ile Ser
                85                  90                  95

Ile Ser Asn Val Ala Leu Ala Asp Glu Gly Glu Tyr Thr Cys Ser Ile
            100                 105                 110

Phe Thr Met Pro Val Arg Thr Ala Lys Ser Leu Val Thr Val Leu Gly
            115                 120                 125

Ile Pro Gln Lys Pro Ile Ile Thr Gly Tyr Lys Ser Ser Leu Arg Glu
130                 135                 140

Lys Asp Thr Ala Thr Leu Asn Cys Gln Ser Ser Gly Ser Lys Pro Ala
145                 150                 155                 160

Ala Arg Leu Thr Trp Arg Lys Gly Asp Gln Glu Leu His Gly Glu Pro
                165                 170                 175

Thr Arg Ile Gln Glu Asp Pro Asn Gly Lys Thr Phe Thr Val Ser Ser
            180                 185                 190

Ser Val Thr Phe Gln Val Thr Arg Glu Asp Asp Gly Ala Ser Ile Val
        195                 200                 205

Cys Ser Val Asn His Glu Ser Leu Lys Gly Ala Asp Arg Ser Thr Ser
        210                 215                 220

Gln Arg Ile Glu Val Leu Tyr Thr Pro Thr Ala Met Ile Arg Pro Asp
225                 230                 235                 240

Pro Pro His Pro Arg Glu Gly Gln Lys Leu Leu Leu His Cys Glu Gly
                245                 250                 255

Arg Gly Asn Pro Val Pro Gln Gln Tyr Leu Trp Glu Lys Glu Gly Ser
            260                 265                 270
```

```
Val Pro Pro Leu Lys Met Thr Gln Glu Ser Ala Leu Ile Phe Pro Phe
            275                 280                 285

Leu Asn Lys Ser Asp Ser Gly Thr Tyr Gly Cys Thr Ala Thr Ser Asn
290                 295                 300

Met Gly Ser Tyr Lys Ala Tyr Tyr Thr Leu Asn Val Asn Asp Pro Ser
305                 310                 315                 320

Pro Val Pro Ser Ser Ser Thr Tyr His Ala Ile Ile Gly Gly Ile
                325                 330                 335

Val Ala Phe Ile Val Phe Leu Leu Ile Met Leu Ile Phe Leu Gly
            340                 345                 350

His Tyr Leu Ile Arg His Lys Gly Thr Tyr Leu Thr His Glu Ala Lys
            355                 360                 365

Gly Ser Asp Asp Ala Pro Asp Ala Asp Thr Ala Ile Ile Asn Ala Glu
370                 375                 380

Gly Gly Gln Ser Gly Gly Asp Asp Lys Lys Glu Tyr Phe Ile
385                 390                 395

<210> SEQ ID NO 13
<211> LENGTH: 350
<212> TYPE: PRT
<213> ORGANISM: homo sapiens

<400> SEQUENCE: 13

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
            35                  40                  45

Glu Met Phe Arg Glu Val Glu Glu Leu Met Glu Asp Thr Gln His Lys
50                  55                  60

Leu Arg Ser Ala Val Glu Glu Met Glu Ala Glu Ala Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Thr Gly Gln Met Val Phe
            115                 120                 125

Ser Glu Thr Val Ile Thr Ser Val Gly Asp Glu Glu Gly Arg Arg Ser
130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
            195                 200                 205

Asp Asn Gln Arg Asp Cys Gln Pro Gly Leu Cys Cys Ala Phe Gln Arg
210                 215                 220

Gly Leu Leu Phe Pro Val Cys Thr Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255
```

Glu Pro Asp Gly Ala Leu Asp Arg Cys Pro Cys Ala Ser Gly Leu Leu
                260                 265                 270

Cys Gln Pro His Ser His Ser Leu Val Tyr Val Cys Lys Pro Thr Phe
            275                 280                 285

Val Gly Ser Arg Asp Gln Asp Gly Glu Ile Leu Leu Pro Arg Glu Val
        290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Arg Glu
                325                 330                 335

Pro Ala Ala Ala Ala Ala Leu Leu Gly Gly Glu Ile
            340                 345                 350

<210> SEQ ID NO 14
<211> LENGTH: 398
<212> TYPE: PRT
<213> ORGANISM: homo sapiens

<400> SEQUENCE: 14

Asn Pro Ala Ser Pro Pro Glu Glu Gly Ser Pro Asp Pro Asp Ser Thr
1               5                   10                  15

Gly Ala Leu Val Glu Glu Glu Asp Pro Phe Phe Lys Val Pro Val Asn
            20                  25                  30

Lys Leu Ala Ala Ala Val Ser Asn Phe Gly Tyr Asp Leu Tyr Arg Val
        35                  40                  45

Arg Ser Ser Met Ser Pro Thr Thr Asn Val Leu Leu Ser Pro Leu Ser
50                  55                  60

Val Ala Thr Ala Leu Ser Ala Leu Ser Leu Gly Ala Asp Glu Arg Thr
65                  70                  75                  80

Glu Ser Ile Ile His Arg Ala Leu Tyr Tyr Asp Leu Ile Ser Ser Pro
                85                  90                  95

Asp Ile His Gly Thr Tyr Lys Glu Leu Leu Asp Thr Val Thr Ala Pro
            100                 105                 110

Gln Lys Asn Leu Lys Ser Ala Ser Arg Ile Val Phe Glu Lys Lys Leu
        115                 120                 125

Arg Ile Lys Ser Ser Phe Val Ala Pro Leu Glu Lys Ser Tyr Gly Thr
130                 135                 140

Arg Pro Arg Val Leu Thr Gly Asn Pro Arg Leu Asp Leu Gln Glu Ile
145                 150                 155                 160

Asn Asn Trp Val Gln Ala Gln Met Lys Gly Lys Leu Ala Arg Ser Thr
                165                 170                 175

Lys Glu Ile Pro Asp Glu Ile Ser Ile Leu Leu Leu Gly Val Ala His
            180                 185                 190

Phe Lys Gly Gln Trp Val Thr Lys Phe Asp Ser Arg Lys Thr Ser Leu
        195                 200                 205

Glu Asp Phe Tyr Leu Asp Glu Glu Arg Thr Val Arg Val Pro Met Met
210                 215                 220

Ser Asp Pro Lys Ala Val Leu Arg Tyr Gly Leu Asp Ser Asp Leu Ser
225                 230                 235                 240

Cys Lys Ile Ala Gln Leu Pro Leu Thr Gly Ser Met Ser Ile Ile Phe
                245                 250                 255

Phe Leu Pro Leu Lys Val Thr Gln Asn Leu Thr Leu Ile Glu Glu Ser
            260                 265                 270

Leu Thr Ser Glu Phe Ile His Asp Ile Asp Arg Glu Leu Lys Thr Val
        275                 280                 285

Gln Ala Val Leu Thr Val Pro Lys Leu Lys Leu Ser Tyr Glu Gly Glu
    290                 295                 300

Val Thr Lys Ser Leu Gln Glu Met Lys Leu Gln Ser Leu Phe Asp Ser
305                 310                 315                 320

Pro Asp Phe Ser Lys Ile Thr Gly Lys Pro Ile Lys Leu Thr Gln Val
                325                 330                 335

Glu His Arg Ala Gly Phe Glu Trp Asn Glu Asp Gly Ala Gly Thr Thr
            340                 345                 350

Pro Ser Pro Gly Leu Gln Pro Ala His Leu Thr Phe Pro Leu Asp Tyr
        355                 360                 365

His Leu Asn Gln Pro Phe Ile Phe Val Leu Arg Asp Thr Asp Thr Gly
    370                 375                 380

Ala Leu Leu Phe Ile Gly Lys Ile Leu Asp Pro Arg Gly Pro
385                 390                 395

<210> SEQ ID NO 15
<211> LENGTH: 474
<212> TYPE: PRT
<213> ORGANISM: homo sapiens

<400> SEQUENCE: 15

Met Lys Arg Val Leu Val Leu Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
    50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
    130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Glu Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
    210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

```
Cys Met Ala Lys Glu Leu Pro Glu His Thr Val Lys Leu Cys Asp Asn
            275                 280                 285

Leu Ser Thr Lys Asn Ser Lys Phe Glu Asp Cys Cys Gln Glu Lys Thr
        290                 295                 300

Ala Met Asp Val Phe Val Cys Thr Tyr Phe Met Pro Ala Ala Gln Leu
305                 310                 315                 320

Pro Glu Leu Pro Asp Val Arg Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
                405                 410                 415

Glu Tyr Lys Lys Lys Leu Ala Glu Arg Leu Lys Ala Lys Leu Pro Glu
            420                 425                 430

Ala Thr Pro Thr Glu Leu Ala Lys Leu Val Asn Lys Arg Ser Asp Phe
        435                 440                 445

Ala Ser Asn Cys Cys Ser Ile Asn Ser Pro Pro Leu Tyr Cys Asp Ser
450                 455                 460

Glu Ile Asp Ala Glu Leu Lys Asn Ile Leu
465                 470

<210> SEQ ID NO 16
<211> LENGTH: 375
<212> TYPE: PRT
<213> ORGANISM: homo sapiens

<400> SEQUENCE: 16

Met Glu Arg Ala Ser Cys Leu Leu Leu Leu Leu Leu Pro Leu Val His
1               5                   10                  15

Val Ser Ala Thr Thr Pro Glu Pro Cys Glu Leu Asp Asp Glu Asp Phe
            20                  25                  30

Arg Cys Val Cys Asn Phe Ser Glu Pro Gln Pro Asp Trp Ser Glu Ala
        35                  40                  45

Phe Gln Cys Val Ser Ala Val Glu Val Glu Ile His Ala Gly Gly Leu
50                  55                  60

Asn Leu Glu Pro Phe Leu Lys Arg Val Asp Ala Asp Ala Asp Pro Arg
65                  70                  75                  80

Gln Tyr Ala Asp Thr Val Lys Ala Leu Arg Val Arg Arg Leu Thr Val
                85                  90                  95

Gly Ala Ala Gln Val Pro Ala Gln Leu Leu Val Gly Ala Leu Arg Val
            100                 105                 110

Leu Ala Tyr Ser Arg Leu Lys Glu Leu Thr Leu Glu Asp Leu Lys Ile
        115                 120                 125

Thr Gly Thr Met Pro Pro Leu Pro Leu Glu Ala Thr Gly Leu Ala Leu
130                 135                 140

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser
                165                 170                 175
```

```
Ile Ala Gln Ala His Ser Pro Ala Phe Ser Cys Glu Gln Val Arg Ala
            180                 185                 190

Phe Pro Ala Leu Thr Ser Leu Asp Leu Ser Asp Asn Pro Gly Leu Gly
            195                 200                 205

Glu Arg Gly Leu Met Ala Ala Leu Cys Pro His Arg Phe Pro Ala Ile
210                 215                 220

Gln Asn Leu Ala Leu Arg Asn Thr Gly Met Glu Thr Pro Thr Gly Val
225                 230                 235                 240

Cys Ala Ala Leu Ala Ala Gly Val Gln Pro His Ser Leu Asp Leu
            245                 250                 255

Ser His Asn Ser Leu Arg Ala Thr Val Asn Pro Ser Ala Pro Arg Cys
            260                 265                 270

Met Trp Ser Ser Ala Leu Asn Ser Leu Asn Leu Ser Phe Ala Gly Leu
            275                 280                 285

Glu Gln Val Pro Lys Gly Leu Pro Ala Lys Leu Arg Val Leu Asp Leu
            290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
            340                 345                 350

Ala Arg Ser Thr Leu Ser Val Gly Val Ser Gly Thr Leu Val Leu Leu
            355                 360                 365

Gln Gly Ala Arg Gly Phe Ala
            370                 375

<210> SEQ ID NO 17
<211> LENGTH: 396
<212> TYPE: PRT
<213> ORGANISM: homo sapiens

<400> SEQUENCE: 17

Met Gly Ala Pro Val Ala Leu Leu Leu Leu Leu Phe Ala Cys Cys
1               5                   10                  15

Trp Ala Pro Ser Gly Ala Asn Leu Ser Gln Asp Asp Ser Gln Pro Trp
            20                  25                  30

Thr Ser Asp Glu Thr Val Val Ala Gly Gly Thr Val Val Leu Lys Cys
            35                  40                  45

Gln Val Lys Asp His Glu Asp Ser Ser Leu Gln Trp Ser Asn Pro Ala
50                  55                  60

Gln Gln Thr Leu Tyr Phe Gly Glu Lys Arg Ala Leu Arg Asp Asn Arg
65                  70                  75                  80

Ile Gln Leu Val Thr Ser Thr Pro His Glu Leu Ser Ile Ser Ile Ser
                85                  90                  95

Asn Val Ala Leu Ala Asp Glu Gly Glu Tyr Thr Cys Ser Ile Phe Thr
            100                 105                 110

Met Pro Val Arg Thr Ala Lys Ser Leu Val Thr Val Leu Gly Ile Pro
            115                 120                 125

Gln Lys Pro Ile Ile Thr Gly Tyr Lys Ser Ser Leu Arg Glu Lys Asp
            130                 135                 140

Thr Ala Thr Leu Asn Cys Gln Ser Ser Gly Ser Lys Pro Ala Ala Arg
145                 150                 155                 160

Leu Thr Trp Arg Lys Gly Asp Gln Glu Leu His Gly Glu Pro Thr Arg
                165                 170                 175
```

Ile Gln Glu Asp Pro Asn Gly Lys Thr Phe Thr Val Ser Ser Ser Val
            180                 185                 190

Thr Phe Gln Val Thr Arg Glu Asp Gly Ala Asn Ile Val Cys Ser
        195                 200                 205

Val Asn His Glu Ser Leu Lys Gly Ala Asp Arg Ser Thr Ser Gln Arg
210                 215                 220

Ile Glu Val Leu Tyr Thr Pro Thr Ala Met Ile Arg Pro Asp Pro Pro
225                 230                 235                 240

His Pro Arg Glu Gly Gln Lys Leu Leu Leu His Cys Glu Gly Arg Gly
            245                 250                 255

Asn Pro Val Pro Gln Gln Tyr Leu Trp Glu Lys Glu Gly Ser Val Pro
            260                 265                 270

Pro Leu Lys Met Thr Gln Glu Ser Ala Leu Ile Phe Pro Phe Leu Asn
            275                 280                 285

Lys Ser Asp Ser Gly Thr Tyr Gly Cys Thr Ala Thr Ser Asn Met Gly
290                 295                 300

Ser Tyr Lys Ala Tyr Tyr Thr Leu Asn Val Asn Asp Pro Ser Pro Val
305                 310                 315                 320

Pro Ser Ser Ser Thr Tyr His Ala Ile Ile Gly Gly Ile Val Ala
            325                 330                 335

Phe Ile Val Phe Leu Leu Leu Ile Met Leu Ile Phe Leu Gly His Tyr
            340                 345                 350

Leu Ile Arg His Lys Gly Thr Tyr Leu Thr His Glu Ala Lys Gly Ser
            355                 360                 365

Asp Asp Ala Pro Asp Ala Asp Thr Ala Ile Ile Asn Ala Glu Gly Gly
            370                 375                 380

Gln Ser Gly Gly Asp Asp Lys Lys Glu Tyr Phe Ile
385                 390                 395

<210> SEQ ID NO 18
<211> LENGTH: 398
<212> TYPE: PRT
<213> ORGANISM: homo sapiens

<400> SEQUENCE: 18

Met Gly Ala Pro Ala Ala Ser Leu Leu Leu Leu Leu Leu Phe Ala
1               5                   10                  15

Cys Cys Trp Ala Pro Gly Gly Ala Asn Leu Ser Gln Asp Asp Ser Gln
            20                  25                  30

Pro Trp Thr Ser Asp Glu Thr Val Ala Gly Gly Thr Val Val Leu
            35                  40                  45

Lys Cys Gln Val Lys Asp His Glu Asp Ser Ser Leu Gln Trp Ser Asn
50                  55                  60

Pro Ala Gln Gln Thr Leu Tyr Phe Gly Glu Lys Arg Ala Leu Arg Asp
65                  70                  75                  80

Asn Arg Ile Gln Leu Val Thr Ser Thr Pro His Glu Leu Ser Ile Ser
            85                  90                  95

Ile Ser Asn Val Ala Leu Ala Asp Glu Gly Glu Tyr Thr Cys Ser Ile
            100                 105                 110

Phe Thr Met Pro Val Arg Thr Ala Lys Ser Leu Val Thr Val Leu Gly
            115                 120                 125

Ile Pro Gln Lys Pro Ile Ile Thr Gly Tyr Lys Ser Ser Leu Arg Glu
            130                 135                 140

Lys Asp Thr Ala Thr Leu Asn Cys Gln Ser Ser Gly Ser Lys Pro Ala
145                 150                 155                 160

Ala Arg Leu Thr Trp Arg Lys Gly Asp Gln Glu Leu His Gly Glu Pro
                165                 170                 175

Thr Arg Ile Gln Glu Asp Pro Asn Gly Lys Thr Phe Thr Val Ser Ser
            180                 185                 190

Ser Val Thr Phe Gln Val Thr Arg Glu Asp Asp Gly Ala Ser Ile Val
        195                 200                 205

Cys Ser Val Asn His Glu Ser Leu Lys Gly Ala Asp Arg Ser Thr Ser
210                 215                 220

Gln Arg Ile Glu Val Leu Tyr Thr Pro Thr Ala Met Ile Arg Pro Asp
225                 230                 235                 240

Pro Pro His Pro Arg Glu Gly Gln Lys Leu Leu His Cys Glu Gly
                245                 250                 255

Arg Gly Asn Pro Val Pro Gln Gln Tyr Leu Trp Glu Lys Glu Gly Ser
                260                 265                 270

Val Pro Pro Leu Lys Met Thr Gln Glu Ser Ala Leu Ile Phe Pro Phe
            275                 280                 285

Leu Asn Lys Ser Asp Ser Gly Thr Tyr Gly Cys Thr Ala Thr Ser Asn
        290                 295                 300

Met Gly Ser Tyr Lys Ala Tyr Tyr Thr Leu Asn Val Asn Asp Pro Ser
305                 310                 315                 320

Pro Val Pro Ser Ser Ser Thr Tyr His Ala Ile Ile Gly Gly Ile
                325                 330                 335

Val Ala Phe Ile Val Phe Leu Leu Leu Ile Met Leu Ile Phe Leu Gly
            340                 345                 350

His Tyr Leu Ile Arg His Lys Gly Thr Tyr Leu Thr His Glu Ala Lys
        355                 360                 365

Gly Ser Asp Asp Ala Pro Asp Ala Asp Thr Ala Ile Ile Asn Ala Glu
    370                 375                 380

Gly Gly Gln Ser Gly Gly Asp Asp Lys Lys Glu Tyr Phe Ile
385                 390                 395

<210> SEQ ID NO 19
<211> LENGTH: 1210
<212> TYPE: PRT
<213> ORGANISM: homo sapiens

<400> SEQUENCE: 19

Arg Ala Met Glu Pro Leu Leu Gly Arg Gly Leu Ile Val Tyr Leu
1               5                   10                  15

Met Phe Leu Leu Leu Lys Phe Ser Lys Ala Ile Glu Ile Pro Ser Ser
            20                  25                  30

Val Gln Gln Val Pro Thr Ile Ile Lys Gln Ser Lys Val Gln Val Ala
        35                  40                  45

Phe Pro Phe Asp Glu Tyr Phe Gln Ile Glu Cys Glu Ala Lys Gly Asn
    50                  55                  60

Pro Glu Pro Thr Phe Ser Trp Thr Lys Asp Gly Asn Pro Phe Tyr Phe
65                  70                  75                  80

Thr Asp His Arg Ile Ile Pro Ser Asn Asn Ser Gly Thr Phe Arg Ile
                85                  90                  95

Pro Asn Glu Gly His Ile Ser His Phe Gln Gly Lys Tyr Arg Cys Phe
            100                 105                 110

Ala Ser Asn Lys Leu Gly Ile Ala Met Ser Glu Glu Ile Glu Phe Ile
        115                 120                 125

Val Pro Ser Val Pro Lys Phe Pro Lys Glu Lys Ile Asp Pro Leu Glu
    130                 135                 140

```
Val Glu Glu Gly Asp Pro Ile Val Leu Pro Cys Asn Pro Pro Lys Gly
145                 150                 155                 160
Leu Pro Pro Leu His Ile Tyr Trp Met Asn Ile Glu Leu Glu His Ile
                165                 170                 175
Glu Gln Asp Glu Arg Val Tyr Met Ser Gln Lys Gly Asp Leu Tyr Phe
            180                 185                 190
Ala Asn Val Glu Glu Lys Asp Ser Arg Asn Asp Tyr Cys Cys Phe Ala
        195                 200                 205
Ala Phe Pro Arg Leu Arg Thr Ile Val Gln Lys Met Pro Met Lys Leu
    210                 215                 220
Thr Val Asn Ser Ser Asn Ser Ile Lys Gln Arg Lys Pro Lys Leu Leu
225                 230                 235                 240
Leu Pro Pro Thr Glu Ser Gly Ser Glu Ser Ser Ile Thr Ile Leu Lys
                245                 250                 255
Gly Glu Ile Leu Leu Leu Glu Cys Phe Ala Glu Gly Leu Pro Thr Pro
                260                 265                 270
Gln Val Asp Trp Asn Lys Ile Gly Gly Asp Leu Pro Lys Gly Arg Glu
            275                 280                 285
Ala Lys Glu Asn Tyr Gly Lys Thr Leu Lys Ile Glu Asn Val Ser Tyr
    290                 295                 300
Gln Asp Lys Gly Asn Tyr Arg Cys Thr Ala Ser Asn Phe Leu Gly Thr
305                 310                 315                 320
Ala Thr His Asp Phe His Val Ile Val Glu Glu Pro Pro Arg Trp Thr
                325                 330                 335
Lys Lys Pro Gln Ser Ala Val Tyr Ser Thr Gly Ser Asn Gly Ile Leu
                340                 345                 350
Leu Cys Glu Ala Glu Gly Glu Pro Gln Pro Thr Ile Lys Trp Arg Val
            355                 360                 365
Asn Gly Ser Pro Val Asp Asn His Pro Phe Ala Gly Asp Val Val Phe
    370                 375                 380
Pro Arg Glu Ile Ser Phe Thr Asn Leu Gln Pro Asn His Thr Ala Val
385                 390                 395                 400
Tyr Gln Cys Glu Ala Ser Asn Val His Gly Thr Ile Leu Ala Asn Ala
                405                 410                 415
Asn Ile Asp Val Val Asp Val Arg Pro Leu Ile Gln Thr Lys Asp Gly
                420                 425                 430
Glu Asn Tyr Ala Thr Val Val Gly Tyr Ser Ala Phe Leu His Cys Glu
            435                 440                 445
Phe Phe Ala Ser Pro Glu Ala Val Ser Trp Gln Lys Val Glu Glu
    450                 455                 460
Val Lys Pro Leu Glu Gly Arg Arg Tyr His Ile Tyr Glu Asn Gly Thr
465                 470                 475                 480
Leu Gln Ile Asn Arg Thr Thr Glu Glu Asp Ala Gly Ser Tyr Ser Cys
                485                 490                 495
Trp Val Glu Asn Ala Ile Gly Lys Thr Ala Val Thr Ala Asn Leu Asp
                500                 505                 510
Ile Arg Asn Ala Thr Lys Leu Arg Val Ser Pro Lys Asn Pro Arg Ile
            515                 520                 525
Pro Lys Leu His Met Leu Glu Leu His Cys Ser Lys Cys Asp Ser
    530                 535                 540
His Leu Lys His Ser Leu Lys Leu Ser Trp Ser Lys Asp Gly Glu Ala
545                 550                 555                 560
Phe Glu Ile Asn Gly Thr Glu Asp Gly Arg Ile Ile Ile Asp Gly Ala
```

```
                565                 570                 575
Asn Leu Thr Ile Ser Asn Val Thr Leu Glu Asp Gln Gly Ile Tyr Cys
            580                 585                 590

Cys Ser Ala His Thr Ala Leu Asp Ser Ala Ala Asp Ile Thr Gln Val
            595                 600                 605

Thr Val Leu Asp Val Pro Asp Pro Glu Asn Leu His Leu Ser Glu
            610                 615                 620

Arg Gln Asn Arg Ser Val Arg Leu Thr Trp Glu Ala Gly Ala Asp His
625                 630                 635                 640

Asn Ser Asn Ile Ser Glu Tyr Ile Val Glu Phe Glu Gly Asn Lys Glu
                645                 650                 655

Glu Pro Gly Arg Trp Glu Glu Leu Thr Arg Val Gln Gly Lys Lys Thr
            660                 665                 670

Thr Val Ile Leu Pro Leu Ala Pro Phe Val Arg Tyr Gln Phe Arg Val
            675                 680                 685

Ile Ala Val Asn Glu Val Gly Arg Ser Gln Pro Ser Gln Pro Ser Asp
            690                 695                 700

His His Glu Thr Pro Pro Ala Ala Pro Asp Arg Asn Pro Gln Asn Ile
705                 710                 715                 720

Arg Val Gln Ala Ser Gln Pro Lys Glu Met Ile Ile Lys Trp Glu Pro
                725                 730                 735

Leu Lys Ser Met Glu Gln Asn Gly Pro Gly Leu Glu Tyr Arg Val Thr
            740                 745                 750

Trp Lys Pro Gln Gly Ala Pro Val Glu Trp Glu Glu Thr Val Thr
            755                 760                 765

Asn His Thr Leu Arg Val Met Thr Pro Ala Val Tyr Ala Pro Tyr Asp
            770                 775                 780

Val Lys Val Gln Ala Ile Asn Gln Leu Gly Ser Gly Pro Asp Pro Gln
785                 790                 795                 800

Ser Val Thr Leu Tyr Ser Gly Glu Asp Tyr Pro Asp Thr Ala Pro Val
            805                 810                 815

Ile His Gly Val Asp Val Ile Asn Ser Thr Leu Val Lys Val Thr Trp
            820                 825                 830

Ser Thr Val Pro Lys Asp Arg Val His Gly Arg Leu Lys Gly Tyr Gln
            835                 840                 845

Ile Asn Trp Trp Lys Thr Lys Ser Leu Leu Asp Gly Arg Thr His Pro
850                 855                 860

Lys Glu Val Asn Ile Leu Arg Phe Ser Gly Gln Arg Asn Ser Gly Met
865                 870                 875                 880

Val Pro Ser Leu Asp Ala Phe Ser Glu Phe His Leu Thr Val Leu Ala
            885                 890                 895

Tyr Asn Ser Lys Gly Ala Gly Pro Glu Ser Glu Pro Tyr Ile Phe Gln
            900                 905                 910

Thr Pro Glu Gly Val Pro Glu Gln Pro Thr Phe Leu Lys Val Ile Lys
            915                 920                 925

Val Asp Lys Asp Thr Ala Thr Leu Ser Trp Gly Leu Pro Lys Lys Leu
930                 935                 940

Asn Gly Asn Leu Thr Gly Tyr Leu Leu Gln Tyr Gln Ile Ile Asn Asp
945                 950                 955                 960

Thr Tyr Glu Ile Gly Glu Leu Asn Asp Ile Asn Ile Thr Thr Pro Ser
                965                 970                 975

Lys Pro Ser Trp His Leu Ser Asn Leu Asn Ala Thr Thr Lys Tyr Lys
            980                 985                 990
```

```
Phe Tyr Leu Arg Ala Cys Thr Ser Gln Gly Cys Gly Lys Pro Ile Thr
        995                 1000                1005

Glu Glu Ser Ser Thr Leu Gly Glu Gly Ser Lys Gly Ile Gly Lys
       1010                 1015                1020

Ile Ser Gly Val Asn Leu Thr Gln Lys Thr His Pro Val Glu Val
       1025                 1030                1035

Phe Glu Pro Gly Ala Glu His Ile Val Arg Leu Met Thr Lys Asn
       1040                 1045                1050

Trp Gly Asp Asn Asp Ser Ile Phe Gln Asp Val Ile Glu Thr Arg
       1055                 1060                1065

Gly Arg Glu Tyr Ala Gly Leu Tyr Asp Asp Ile Ser Thr Gln Gly
       1070                 1075                1080

Trp Phe Ile Gly Leu Met Cys Ala Ile Ala Leu Leu Thr Leu Leu
       1085                 1090                1095

Leu Leu Thr Val Cys Phe Val Lys Arg Asn Arg Gly Gly Lys Tyr
       1100                 1105                1110

Ser Val Lys Glu Lys Glu Asp Leu His Pro Asp Pro Glu Ile Gln
       1115                 1120                1125

Ser Val Lys Asp Glu Thr Phe Gly Glu Tyr Ser Asp Ser Asp Glu
       1130                 1135                1140

Lys Pro Leu Lys Gly Ser Leu Arg Ser Leu Asn Arg Asp Met Gln
       1145                 1150                1155

Pro Thr Glu Ser Ala Asp Ser Leu Val Glu Tyr Gly Glu Gly Asp
       1160                 1165                1170

His Gly Leu Phe Ser Glu Asp Gly Ser Phe Ile Gly Ala Tyr Ala
       1175                 1180                1185

Gly Ser Lys Glu Lys Gly Ser Val Glu Ser Asn Gly Ser Ser Thr
       1190                 1195                1200

Ala Thr Phe Pro Leu Arg Ala
       1205                 1210

<210> SEQ ID NO 20
<211> LENGTH: 449
<212> TYPE: PRT
<213> ORGANISM: homo sapiens

<400> SEQUENCE: 20

Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
        35                  40                  45

Ala Val Asn Gly Val Lys Gln Ile Lys Thr Leu Ile Glu Lys Thr Asn
    50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
    130                 135                 140
```

```
Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
            165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
            195                 200                 205

Phe Ser Leu Pro His Arg Arg Pro His Phe Phe Pro Lys Ser Leu
210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
            245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
            275                 280                 285

Arg His Asn Ser Thr Gly Cys Leu Arg Met Lys Asp Gln Cys Asp Lys
290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
            325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
            355                 360                 365

Val Ser Arg Leu Ala Asn Leu Thr Gln Gly Glu Asp Gln Tyr Tyr Leu
            370                 375                 380

Arg Val Thr Thr Val Ala Ser His Thr Ser Asp Ser Asp Val Pro Ser
385                 390                 395                 400

Gly Val Thr Glu Val Val Lys Leu Phe Gly Ser Asp Pro Ile Thr
            405                 410                 415

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
            435                 440                 445

Glu

<210> SEQ ID NO 21
<211> LENGTH: 274
<212> TYPE: PRT
<213> ORGANISM: homo sapiens

<400> SEQUENCE: 21

Met Gln Asp His Phe Ser Arg Ala Ser Ser Ile Ile Asp Glu Leu Phe
1               5                   10                  15

Gln Asp Arg Phe Phe Thr Arg Glu Pro Gln Asp Thr Tyr His Tyr Leu
            20                  25                  30

Pro Phe Ser Leu Pro His Arg Arg Pro His Phe Phe Pro Lys Ser
            35                  40                  45

Arg Ile Val Arg Ser Leu Met Pro Phe Ser Pro Tyr Glu Pro Leu Asn
    50                  55                  60

Phe His Ala Met Phe Gln Pro Phe Leu Glu Met Ile His Glu Ala Gln
```

```
                65                  70                  75                  80
Gln Ala Met Asp Ile His Phe His Ser Pro Ala Phe Gln His Pro Pro
                        85                  90                  95
Thr Glu Phe Ile Arg Glu Gly Asp Asp Arg Thr Val Cys Arg Glu
                100                 105                 110
Ile Arg His Asn Ser Thr Gly Cys Leu Arg Met Lys Asp Gln Cys Asp
                115                 120                 125
Lys Cys Arg Glu Ile Leu Ser Val Asp Cys Ser Thr Asn Asn Pro Ser
130                 135                 140
Gln Ala Lys Leu Arg Arg Glu Leu Asp Glu Ser Leu Gln Val Ala Glu
145                 150                 155                 160
Arg Leu Thr Arg Lys Tyr Asn Glu Leu Leu Lys Ser Tyr Gln Trp Lys
                165                 170                 175
Met Leu Asn Thr Ser Ser Leu Leu Glu Gln Leu Asn Glu Gln Phe Asn
                180                 185                 190
Trp Val Ser Arg Leu Ala Asn Leu Thr Gln Gly Glu Asp Gln Tyr Tyr
                195                 200                 205
Leu Arg Val Thr Thr Val Ala Ser His Thr Ser Asp Ser Asp Val Pro
210                 215                 220
Ser Gly Val Thr Glu Val Val Lys Leu Phe Asp Ser Asp Pro Ile
225                 230                 235                 240
Thr Val Thr Val Pro Val Glu Val Ser Arg Lys Asn Pro Lys Phe Met
                245                 250                 255
Glu Thr Val Ala Glu Lys Ala Leu Gln Glu Tyr Arg Lys Lys His Arg
                260                 265                 270
Glu Glu

<210> SEQ ID NO 22
<211> LENGTH: 253
<212> TYPE: PRT
<213> ORGANISM: homo sapiens

<400> SEQUENCE: 22

Gly Ser Ser Glu His Leu Lys Arg Glu His Ser Leu Ile Lys Pro Tyr
1               5                   10                  15
Gln Gly Val Gly Ser Ser Met Pro Leu Trp Asp Phe Gln Gly Ser
                20                  25                  30
Thr Ile Leu Thr Ser Gln Tyr Val Arg Leu Thr Pro Asp Glu Arg Ser
                35                  40                  45
Lys Glu Gly Ser Ile Trp Asn His Gln Pro Cys Phe Leu Lys Asp Trp
50                  55                  60
Glu Met His Val His Phe Lys Val His Gly Thr Gly Lys Lys Asn Leu
65                  70                  75                  80
His Gly Asp Gly Ile Ala Leu Trp Tyr Thr Arg Asp Arg Leu Val Pro
                85                  90                  95
Gly Pro Val Phe Gly Ser Lys Asp Asn Phe His Gly Leu Ala Ile Phe
                100                 105                 110
Leu Asp Thr Tyr Pro Asn Asp Glu Thr Thr Glu Arg Val Phe Pro Tyr
                115                 120                 125
Ile Ser Val Met Val Asn Asn Gly Ser Leu Ser Tyr Asp His Ser Lys
                130                 135                 140
Asp Gly Arg Trp Thr Glu Leu Ala Gly Cys Thr Ala Asp Phe Arg Asn
145                 150                 155                 160
Arg Asp His Asp Thr Phe Leu Ala Val Arg Tyr Ser Arg Gly Arg Leu
                165                 170                 175
```

```
Thr Val Met Thr Asp Leu Glu Asp Lys Asn Glu Trp Lys Asn Cys Ile
            180                 185                 190

Asp Ile Thr Gly Val Arg Leu Pro Thr Gly Tyr Tyr Phe Gly Ala Ser
            195                 200                 205

Ala Gly Thr Gly Asp Leu Ser Asp Asn His Asp Ile Ile Ser Met Lys
        210                 215                 220

Leu Phe Gln Leu Met Val Glu His Thr Pro Asp Glu Glu Asn Ile Asp
225                 230                 235                 240

Trp Thr Lys Ile Glu Pro Ser Val Asn Phe Leu Lys Ser
                245                 250

<210> SEQ ID NO 23
<211> LENGTH: 501
<212> TYPE: PRT
<213> ORGANISM: homo sapiens

<400> SEQUENCE: 23

Met Gln Val Cys Ser Gln Pro Gln Arg Gly Cys Val Arg Glu Gln Ser
1               5                   10                  15

Ala Ile Asn Thr Ala Pro Pro Ser Ala His Asn Ala Ala Ser Pro Gly
            20                  25                  30

Gly Ala Arg Gly His Arg Val Pro Leu Thr Glu Ala Cys Lys Asp Ser
        35                  40                  45

Arg Ile Gly Gly Met Met Lys Thr Leu Leu Leu Phe Val Gly Leu Leu
    50                  55                  60

Leu Thr Trp Glu Ser Gly Gln Val Leu Gly Asp Gln Thr Val Ser Asp
65                  70                  75                  80

Asn Glu Leu Gln Glu Met Ser Asn Gln Gly Ser Lys Tyr Val Asn Lys
                85                  90                  95

Glu Ile Gln Asn Ala Val Asn Gly Val Lys Gln Ile Lys Thr Leu Ile
            100                 105                 110

Glu Lys Thr Asn Glu Glu Arg Lys Thr Leu Leu Ser Asn Leu Glu Glu
        115                 120                 125

Ala Lys Lys Lys Lys Glu Asp Ala Leu Asn Glu Thr Arg Glu Ser Glu
    130                 135                 140

Thr Lys Leu Lys Glu Leu Pro Gly Val Cys Asn Glu Thr Met Met Ala
145                 150                 155                 160

Leu Trp Glu Glu Cys Lys Pro Cys Leu Lys Gln Thr Cys Met Lys Phe
                165                 170                 175

Tyr Ala Arg Val Cys Arg Ser Gly Ser Gly Leu Val Gly Arg Gln Leu
            180                 185                 190

Glu Glu Phe Leu Asn Gln Ser Ser Pro Phe Tyr Phe Trp Met Asn Gly
        195                 200                 205

Asp Arg Ile Asp Ser Leu Leu Glu Asn Asp Arg Gln Gln Thr His Met
    210                 215                 220

Leu Asp Val Met Gln Asp His Phe Ser Arg Ala Ser Ser Ile Ile Asp
225                 230                 235                 240

Glu Leu Phe Gln Asp Arg Phe Phe Thr Arg Glu Pro Gln Asp Thr Tyr
                245                 250                 255

His Tyr Leu Pro Phe Ser Leu Pro His Arg Arg Pro His Phe Phe Phe
            260                 265                 270

Pro Lys Ser Arg Ile Val Arg Ser Leu Met Pro Phe Ser Pro Tyr Glu
        275                 280                 285

Pro Leu Asn Phe His Ala Met Phe Gln Pro Phe Leu Glu Met Ile His
    290                 295                 300
```

```
Glu Ala Gln Gln Ala Met Asp Ile His Phe His Ser Pro Ala Phe Gln
305                 310                 315                 320

His Pro Pro Thr Glu Phe Ile Arg Glu Gly Asp Asp Arg Thr Val
            325                 330                 335

Cys Arg Glu Ile Arg His Asn Ser Thr Gly Cys Leu Arg Met Lys Asp
            340                 345                 350

Gln Cys Asp Lys Cys Arg Glu Ile Leu Ser Val Asp Cys Ser Thr Asn
        355                 360                 365

Asn Pro Ser Gln Ala Lys Leu Arg Arg Glu Leu Asp Glu Ser Leu Gln
    370                 375                 380

Val Ala Glu Arg Leu Thr Arg Lys Tyr Asn Glu Leu Leu Lys Ser Tyr
385                 390                 395                 400

Gln Trp Lys Met Leu Asn Thr Ser Ser Leu Leu Glu Gln Leu Asn Glu
            405                 410                 415

Gln Phe Asn Trp Val Ser Arg Leu Ala Asn Leu Thr Gln Gly Glu Asp
            420                 425                 430

Gln Tyr Tyr Leu Arg Val Thr Thr Val Ala Ser His Thr Ser Asp Ser
        435                 440                 445

Asp Val Pro Ser Gly Val Thr Glu Val Val Lys Leu Phe Asp Ser
    450                 455                 460

Asp Pro Ile Thr Val Thr Val Pro Val Glu Val Ser Arg Lys Asn Pro
465                 470                 475                 480

Lys Phe Met Glu Thr Val Ala Glu Lys Ala Leu Gln Glu Tyr Arg Lys
            485                 490                 495

Lys His Arg Glu Glu
            500

<210> SEQ ID NO 24
<211> LENGTH: 240
<212> TYPE: PRT
<213> ORGANISM: homo sapiens

<400> SEQUENCE: 24

Met Leu Ala Leu Leu Cys Ser Cys Leu Leu Leu Ala Ala Gly Ala Ser
1               5                   10                  15

Asp Ala Trp Thr Gly Glu Asp Ser Ala Glu Pro Asn Ser Asp Ser Ala
            20                  25                  30

Glu Trp Ile Arg Asp Met Tyr Ala Lys Val Thr Glu Ile Trp Gln Glu
        35                  40                  45

Val Met Gln Arg Arg Asp Asp Gly Ala Leu His Ala Ala Cys Gln
50                  55                  60

Val Gln Pro Ser Ala Thr Leu Asp Ala Ala Gln Pro Arg Val Thr Gly
65                  70                  75                  80

Val Val Leu Phe Arg Gln Leu Ala Pro Arg Ala Lys Leu Asp Ala Phe
                85                  90                  95

Phe Ala Leu Glu Gly Phe Pro Thr Glu Pro Asn Ser Ser Ser Arg Ala
            100                 105                 110

Ile His Val His Gln Phe Gly Asp Leu Ser Gln Gly Cys Glu Ser Thr
        115                 120                 125

Gly Pro His Tyr Asn Pro Leu Ala Val Pro His Pro Gln His Pro Gly
    130                 135                 140

Asp Phe Gly Asn Phe Ala Val Arg Asp Gly Ser Leu Trp Arg Tyr Arg
145                 150                 155                 160

Ala Gly Leu Ala Ala Ser Leu Ala Gly Pro His Ser Ile Val Gly Arg
                165                 170                 175
```

```
Ala Val Val His Ala Gly Glu Asp Asp Leu Gly Arg Gly Gly Asn
        180                 185                 190

Gln Ala Ser Val Glu Asn Gly Asn Ala Gly Arg Arg Leu Ala Cys Cys
        195                 200                 205

Val Val Gly Val Cys Gly Pro Gly Leu Trp Glu Arg Gln Ala Arg Glu
    210                 215                 220

His Ser Glu Arg Lys Lys Arg Arg Glu Ser Glu Cys Lys Ala Ala
225                 230                 235                 240

<210> SEQ ID NO 25
<211> LENGTH: 134
<212> TYPE: PRT
<213> ORGANISM: homo sapiens

<400> SEQUENCE: 25

Asp Leu Gly Thr Leu Ser Gly Ile Gly Thr Leu Asp Gly Phe Arg His
1               5                   10                  15

Arg His Pro Asp Glu Ala Ala Phe Phe Asp Thr Ala Ser Thr Gly Lys
            20                  25                  30

Thr Phe Pro Gly Phe Phe Ser Pro Met Leu Gly Glu Phe Val Ser Glu
        35                  40                  45

Thr Glu Ser Arg Gly Ser Glu Ser Gly Ile Phe Thr Asn Thr Lys Glu
    50                  55                  60

Ser Ser His His Pro Gly Ile Ala Glu Phe Pro Ser Arg Gly Lys
65              70                  75                  80

Ser Ser Ser Tyr Ser Lys Gln Phe Thr Ser Thr Ser Tyr Asn Arg
                85                  90                  95

Gly Asp Ser Thr Phe Glu Ser Lys Ser Tyr Lys Met Ala Asp Glu Ala
            100                 105                 110

Gly Ser Glu Ala Asp His Glu Gly Thr His Ser Thr Lys Arg Gly His
        115                 120                 125

Ala Lys Ser Arg Pro Val
        130

<210> SEQ ID NO 26
<211> LENGTH: 223
<212> TYPE: PRT
<213> ORGANISM: homo sapiens

<400> SEQUENCE: 26

Leu Val His Gly Gly Pro Cys Asp Lys Thr Ser His Pro Tyr Gln Ala
1               5                   10                  15

Ala Leu Tyr Thr Ser Gly His Leu Leu Cys Gly Gly Val Leu Ile His
            20                  25                  30

Pro Leu Trp Val Leu Thr Ala Ala His Cys Lys Lys Pro Asn Leu Gln
        35                  40                  45

Val Phe Leu Gly Lys His Asn Leu Arg Gln Arg Glu Ser Ser Gln Glu
    50                  55                  60

Gln Ser Ser Val Val Arg Ala Val Ile His Pro Asp Tyr Asp Ala Ala
65              70                  75                  80

Ser His Asp Gln Asp Ile Met Leu Leu Arg Leu Ala Arg Pro Ala Lys
                85                  90                  95

Leu Ser Glu Leu Ile Gln Pro Leu Pro Leu Glu Arg Asp Cys Ser Ala
            100                 105                 110

Asn Thr Thr Ser Cys His Ile Leu Gly Trp Gly Lys Thr Ala Asp Gly
        115                 120                 125
```

Asp Phe Pro Asp Thr Ile Gln Cys Ala Tyr Ile His Leu Val Ser Arg
    130                 135                 140

Glu Glu Cys Glu His Ala Tyr Pro Gly Gln Ile Thr Gln Asn Met Leu
145                 150                 155                 160

Cys Ala Gly Asp Glu Lys Tyr Gly Lys Asp Ser Cys Gln Gly Asp Ser
                165                 170                 175

Gly Gly Pro Leu Val Cys Gly Asp His Leu Arg Gly Leu Val Ser Trp
            180                 185                 190

Gly Asn Ile Pro Cys Gly Ser Lys Glu Lys Pro Gly Val Tyr Thr Asn
        195                 200                 205

Val Cys Arg Tyr Thr Asn Trp Ile Gln Lys Thr Ile Gln Ala Lys
    210                 215                 220

<210> SEQ ID NO 27
<211> LENGTH: 204
<212> TYPE: PRT
<213> ORGANISM: homo sapiens

<400> SEQUENCE: 27

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val
        195                 200

<210> SEQ ID NO 28
<211> LENGTH: 227
<212> TYPE: PRT
<213> ORGANISM: homo sapiens

<400> SEQUENCE: 28

Met Arg Val Ala Gly Ala Ala Lys Leu Val Val Ala Val Ala Val Phe
1               5                   10                  15

Leu Leu Thr Phe Tyr Val Ile Ser Gln Val Phe Glu Ile Lys Met Asp
            20                  25                  30

Ala Ser Leu Gly Asn Leu Phe Ala Arg Ser Ala Leu Asp Thr Ala Ala

```
                 35                  40                  45
His Ser Thr Lys Pro Pro Arg Tyr Lys Cys Gly Ile Ser Lys Ala Cys
 50                  55                  60

Pro Glu Lys His Phe Ala Phe Lys Met Ala Ser Gly Ala Ala Asn Val
 65                  70                  75                  80

Val Gly Pro Lys Ile Cys Leu Glu Asp Asn Val Leu Met Ser Gly Val
                 85                  90                  95

Lys Asn Asn Val Gly Arg Gly Ile Asn Val Ala Leu Ala Asn Gly Lys
                100                 105                 110

Thr Gly Glu Val Leu Asp Thr Lys Tyr Phe Asp Met Trp Gly Gly Asp
                115                 120                 125

Val Ala Pro Phe Ile Glu Phe Leu Lys Ala Ile Gln Asp Gly Thr Ile
130                 135                 140

Val Leu Met Gly Thr Tyr Asp Asp Gly Ala Thr Lys Leu Asn Asp Glu
145                 150                 155                 160

Ala Arg Arg Leu Ile Ala Asp Leu Gly Ser Thr Ser Ile Thr Asn Leu
                165                 170                 175

Gly Phe Arg Asp Asn Trp Val Phe Cys Gly Gly Lys Gly Ile Lys Thr
                180                 185                 190

Lys Ser Pro Phe Glu Gln His Ile Lys Asn Asn Lys Asp Thr Asn Lys
                195                 200                 205

Tyr Glu Gly Trp Pro Glu Val Val Glu Met Glu Gly Cys Ile Pro Gln
                210                 215                 220

Lys Gln Asp
225

<210> SEQ ID NO 29
<211> LENGTH: 398
<212> TYPE: PRT
<213> ORGANISM: homo sapiens

<400> SEQUENCE: 29

Met Gly Ala Pro Ala Ala Ser Leu Leu Leu Leu Leu Leu Leu Phe Ala
  1                   5                  10                  15

Cys Cys Trp Ala Pro Gly Gly Ala Asn Leu Ser Gln Asp Asp Ser Gln
                 20                  25                  30

Pro Trp Thr Ser Asp Glu Thr Val Val Ala Gly Gly Thr Val Val Leu
                 35                  40                  45

Lys Cys Gln Val Lys Asp His Glu Asp Ser Ser Leu Gln Trp Ser Asn
 50                  55                  60

Pro Ala Gln Gln Thr Leu Tyr Phe Gly Glu Lys Arg Ala Leu Arg Asp
 65                  70                  75                  80

Asn Arg Ile Gln Leu Val Thr Ser Thr Pro His Glu Leu Ser Ile Ser
                 85                  90                  95

Ile Ser Asn Val Ala Leu Ala Asp Glu Gly Glu Tyr Thr Cys Ser Ile
                100                 105                 110

Phe Thr Met Pro Val Arg Thr Ala Lys Ser Leu Val Thr Val Leu Gly
                115                 120                 125

Ile Pro Gln Lys Pro Ile Ile Thr Gly Tyr Lys Ser Ser Leu Arg Glu
130                 135                 140

Lys Asp Thr Ala Thr Leu Asn Cys Gln Ser Ser Gly Ser Lys Pro Ala
145                 150                 155                 160

Ala Arg Leu Thr Trp Arg Lys Gly Asp Gln Glu Leu His Gly Glu Pro
                165                 170                 175

Thr Arg Ile Gln Glu Asp Pro Asn Gly Lys Thr Phe Thr Val Ser Ser
```

-continued

```
            180                 185                 190
Ser Val Thr Phe Gln Val Thr Arg Glu Asp Asp Gly Ala Ser Ile Val
        195                 200                 205

Cys Ser Val Asn His Glu Ser Leu Lys Gly Ala Asp Arg Ser Thr Ser
        210                 215                 220

Gln Arg Ile Glu Val Leu Tyr Thr Pro Thr Ala Met Ile Arg Pro Asp
225                 230                 235                 240

Pro Pro His Pro Arg Glu Gly Gln Lys Leu Leu Leu His Cys Glu Gly
                245                 250                 255

Arg Gly Asn Pro Val Pro Gln Gln Tyr Leu Trp Glu Lys Glu Gly Ser
                260                 265                 270

Val Pro Pro Leu Lys Met Thr Gln Glu Ser Ala Leu Ile Phe Pro Phe
                275                 280                 285

Leu Asn Lys Ser Asp Ser Gly Thr Tyr Gly Cys Thr Ala Thr Ser Asn
        290                 295                 300

Met Gly Ser Tyr Lys Ala Tyr Tyr Thr Leu Asn Val Asn Asp Pro Ser
305                 310                 315                 320

Pro Val Pro Ser Ser Ser Thr Tyr His Ala Ile Ile Gly Gly Ile
                325                 330                 335

Val Ala Phe Ile Val Phe Leu Leu Leu Ile Met Leu Ile Phe Leu Gly
                340                 345                 350

His Tyr Leu Ile Arg His Lys Gly Thr Tyr Leu Thr His Glu Ala Lys
        355                 360                 365

Gly Ser Asp Asp Ala Pro Asp Ala Asp Thr Ala Ile Ile Asn Ala Glu
    370                 375                 380

Gly Gly Gln Ser Gly Gly Asp Asp Lys Lys Glu Tyr Phe Ile
385                 390                 395
```